(12) United States Patent
Kobayashi et al.

(10) Patent No.: US 6,930,706 B2
(45) Date of Patent: Aug. 16, 2005

(54) ORGAN-REGION-INDICATION SYSTEM INCORPORATED IN ELECTRONIC ENDOSCOPE SYSTEM

(75) Inventors: Hiroyuki Kobayashi, Saitama (JP); Hideo Sugimoto, Tokyo (JP)

(73) Assignee: PENTAX Corporation, Tokyo (JP)

( * ) Notice: Subject to any disclaimer, the term of this patent is extended or adjusted under 35 U.S.C. 154(b) by 500 days.

(21) Appl. No.: 10/082,210

(22) Filed: Feb. 26, 2002

(65) Prior Publication Data

US 2002/0118278 A1 Aug. 29, 2002

(30) Foreign Application Priority Data

Feb. 28, 2001 (JP) ..................................... P2001-054048

(51) Int. Cl.[7] .............................................. H04B 1/66
(52) U.S. Cl. ............................. 348/65; 348/68; 348/74; 348/75; 600/109; 600/112; 600/118; 600/114
(58) Field of Search ............................. 348/65, 74, 77, 348/163, 68, 75; 600/109, 114, 112, 118

(56) References Cited

U.S. PATENT DOCUMENTS 5,124,789 A * 6/1992 Hiyama et al. ............... 348/74
5,592,216 A * 1/1997 Uehara et al. ............... 348/74

* cited by examiner

*Primary Examiner*—Shawn S. An
(74) *Attorney, Agent, or Firm*—Greenblum & Bernstein, P.L.C.

(57) ABSTRACT

In an organ-region-indication system incorporated in an electronic endoscope system in which an endoscope image is displayed as a motion image on a monitor in accordance with a video signal produced therein, an organ-region-image data base is formed based on an organ map. A plurality of reference data indicating organ-regions and a plurality of image data representing the organ-region are correspondingly stored in the data base. Still image data is retrieved as referential image data from the video signal at suitable regular time intervals. The data base is searched for image data which coincides with the referential image data after the retrieval of the still image data. Corresponding reference data is displayed on the monitor only when the image data, which coincides with the referential image data, is found by the searching.

9 Claims, 15 Drawing Sheets

FIG. 4

| BRONCHUS-REGION-IMAGE DATA BASE | | | | | |
|---|---|---|---|---|---|
| LEFT-MAIN-BRANCH-REGION-IMAGE DATA BASE SECTION | $L-B^{10}$ | IMAGE-DATA STORAGE AREA | ⋮ | | |
| | $L-B^9$ | IMAGE-DATA STORAGE AREA | | | |
| | $L-B^8$ | IMAGE-DATA STORAGE AREA | $R-L^6c$ | IMAGE-DATA STORAGE AREA |
| | ⋮ | ⋮ | $L-B^6b$ | IMAGE-DATA STORAGE AREA |
| | | | $L-B^6a$ | IMAGE-DATA STORAGE AREA |
| | $L-B^3$ | IMAGE-DATA STORAGE AREA | ⋮ | ⋮ |
| | $L-B^2$ | IMAGE-DATA STORAGE AREA | | |
| | $L-B^1$ | IMAGE-DATA STORAGE AREA | | |
| RIGHT-MAIN-BRANCH-REGION-IMAGE DATA BASE SECTION | $R-B^{10}$ | IMAGE-DATA STORAGE AREA | ⋮ | ⋮ |
| | $R-B^9$ | IMAGE-DATA STORAGE AREA | | |
| | $R-B^8$ | IMAGE-DATA STORAGE AREA | $R-B^6c$ | IMAGE-DATA STORAGE AREA |
| | ⋮ | ⋮ | $R-B^6b$ | IMAGE-DATA STORAGE AREA |
| | | | $R-B^6a$ | IMAGE-DATA STORAGE AREA |
| | $R-B^3$ | IMAGE-DATA STORAGE AREA | ⋮ | ⋮ |
| | $R-B^2$ | IMAGE-DATA STORAGE AREA | | |
| | $R-B^1$ | IMAGE-DATA STORAGE AREA | | |

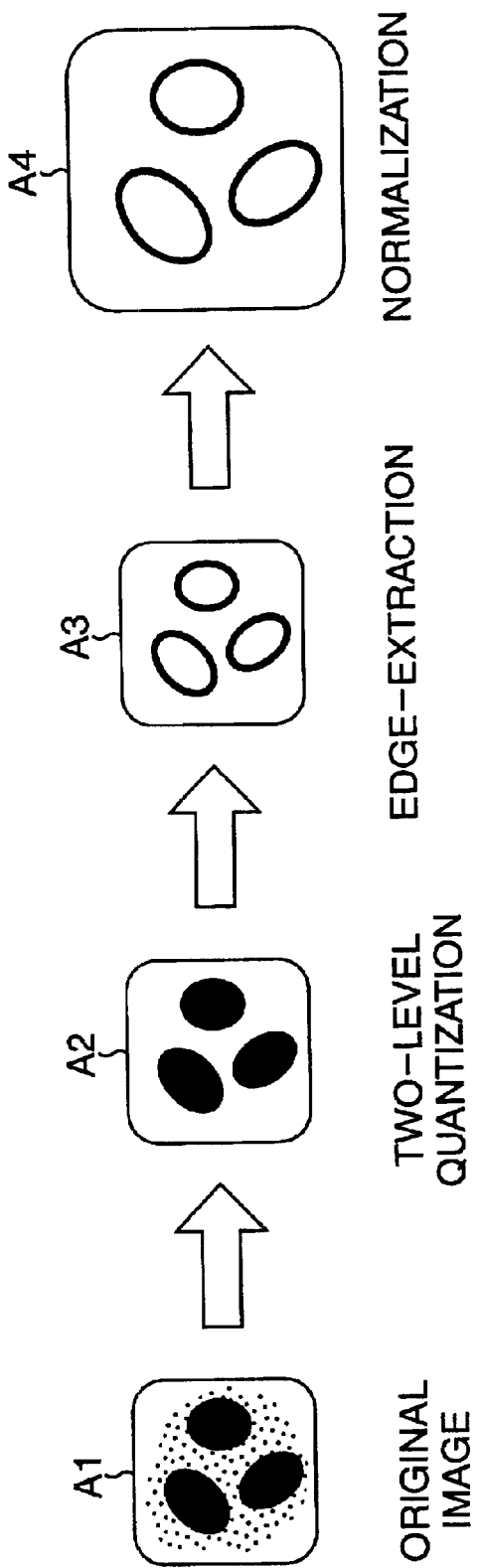

ORGAN-REGION-INDICATION SYSTEM INCORPORATED IN ELECTRONIC ENDOSCOPE SYSTEM

BACKGROUND OF THE INVENTION

1. Field of the Invention

The present invention generally relates to an electronic endoscope system, and, in particular, is directed to the development of an electronic endoscope system in which a region of an organ of a human body is indicated during medical examination of the organ using the electronic endoscope system.

2. Description of the Related Art

As is well known, an electronic endoscope system is utilized to medically examine internal organs of a human body, such as, the esophagus, stomach, bronchi, lungs, and so on. In general, the electronic endoscope system includes a scope having a solid-state image sensor provided at a distal end thereof, an image-signal-processing unit to which the scope is detachably coupled, and a TV monitor connected to the image-signal-processing unit.

When the scope is inserted in an internal organ of a human body, the solid-state image sensor optically photographs an endoscope image, and converts the photographed image into a frame of image-pixel signals. The frame of image-pixel signals is repeatedly read from the solid-state image sensor at a given regular time interval, and is fed to the image-signal-processing unit. The image-signal-processing unit produces a video signal on the basis of the frames of image-pixel signals obtained from the solid-state image sensor, and feeds the video signal to the TV monitor. The TV monitor reproduces the endoscope image as a motion picture in accordance with the video signal.

Before the medical examination can be precisely and promptly performed, it is necessary for a doctor to correctly and quickly determine what region of the organ is being reproduced on the TV monitor, i.e., what region of the organ the distal end of the scope has reached. However, the correct and quick determination of the region of the organ reproduced on the TV monitor is very difficult, especially for a novice who manipulates the scope. Also, when a complex organ, such as the bronchi, is examined using the electronic endoscope system, it is difficult for even a skilful doctor to correctly and quickly determine what region of the complex organ is being reproduced on the TV monitor, i.e., what region of the complex organ the distal end of the scope has reached.

SUMMARY OF THE INVENTION

Therefore, an object of the present invention is to provide a novel organ-region-indication system incorporated in an electronic endoscope system to indicate what region of an organ of the human body is being reproduced on a TV monitor during a medical examination of the organ, using the electronic endoscope system.

In accordance with the present invention, there is provided an organ-region-indication system incorporated in an electronic endoscope system in which an endoscope image is displayed as a motion image on a monitor in accordance with a video signal produced therein. In the organ-region-indication system, there is an organ-region-image data base which is constituted on the basis of an organ map. A plurality of reference data, indicating distinctive organ-regions and a plurality of image data, representing the distinctive organ-region, are correspondingly stored in the organ-region-image data base. A still-image-capturing system retrieves a frame of still image data as referential image data from the video signal at suitable regular time intervals. A searching system searches the organ-region-image data base for image data which coincides with the referential image data, after the retrieval of a frame of still image data from the video signal, by the still-image-capturing system. A reference-data-display-controlling system displays corresponding reference data on the monitor only when the image data, which coincides with the referential image data, is found by the searching system. In other words, an endoscope image displayed as a motion image on the monitor is identified by the corresponding reference data displayed thereon.

The reference-data-display-controlling system preferably comprises a canceling system that cancels a preceding display of reference data on the monitor when the image data, which coincides with the referential image data, is not found by the searching system.

Also, the reference-data-display-controlling system may comprise a forcible-canceling system that forcibly cancels a display of the reference data on the monitor even if the image data, which coincides with the referential image data, is found by the searching system.

Preferably, the searching system comprises a searching-area-designating system that designates an area to be searched in the organ-region-image data base.

The organ-region-indication system may further comprise a data-base-renovating system that renovates the organ-region-image data base on the basis of the referential image data when the image data coincides with the referential image data.

Preferably, the searching system comprises a reading system that reads image data in succession from the organ-region-image data base, and a determining system that determines whether the read image data coincides with the referential image data.

Also, preferably, the determining system comprises a numerical-evaluating system that numerically evaluates the degree of coincidence between the read image data and the referential image data, and a comparing system that compares the degree of coincidence with a threshold. When the degree of coincidence is more than the threshold, it is determined that there is a coincidence between the read image data and the referential image data. When the degree of coincidence is less that the threshold, it is determined that there is no coincidence between the read image data and the referential image data. The determining system may comprise a threshold-altering system that alters a value of the threshold.

Further, preferably, each image data, to be stored in said organ-region-image data base, is subjected to feature-extraction, such as edge-extraction, and the referential image data is subjected to the same feature-extraction as each image data.

BRIEF DESCRIPTION OF THE DRAWINGS

The object and other objects of the present invention will be better understood from the following descriptions, with reference to the accompanying drawings, in which:

FIG. 4 is a conceptual view of a bronchus-region-image data base constituted in an EEPROM shown in FIG. 2;

FIG. 5 is a conceptual view showing a processing of still image data to be stored in the bronchus-region-image data base;

DESCRIPTION OF THE PREFERRED EMBODIMENTS

Figure 1:
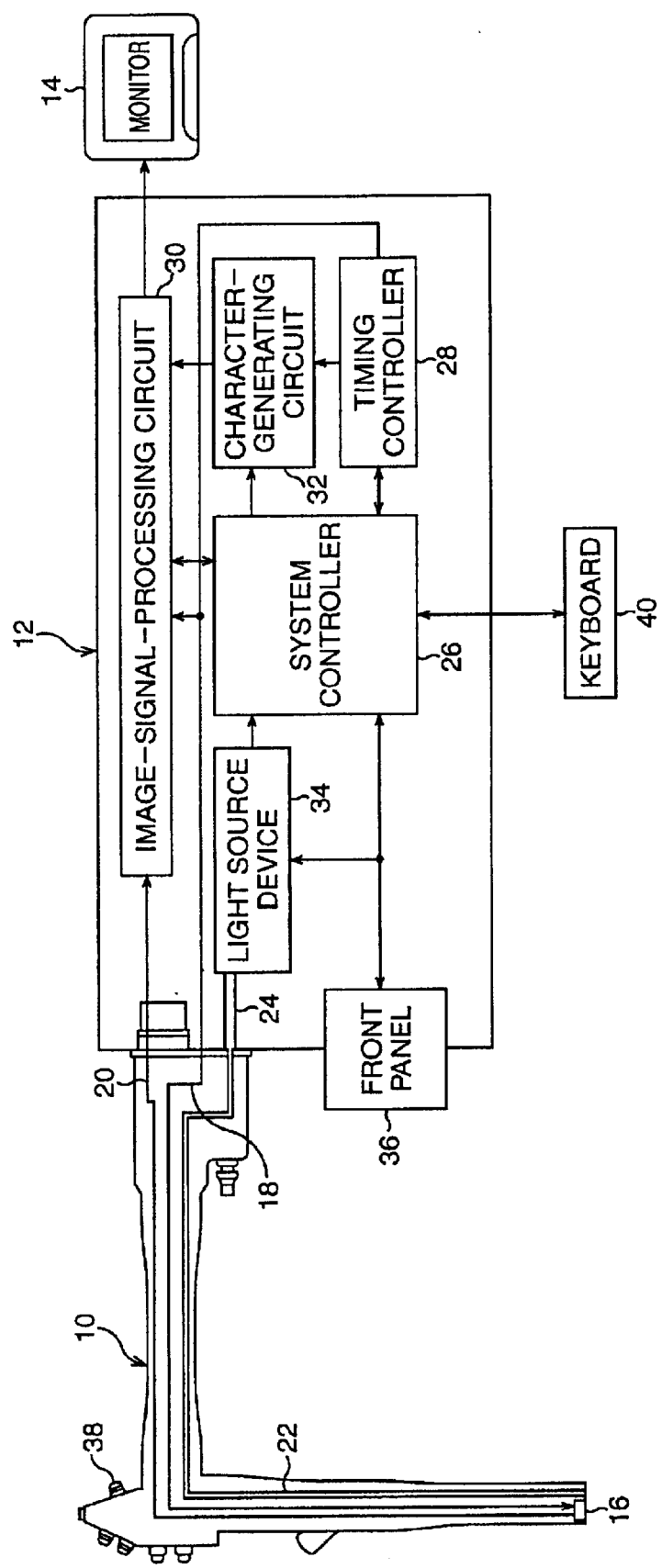
FIG. 1 is a schematic view showing the entire electronic endoscope system incorporating an organ-region-indication system according to the present invention.

FIG. 1 schematically shows an electronic endoscope system in which an organ-region-indication system according to the present invention is incorporated. The electronic endoscope system comprises a scope 10, an image-signal processing unit (a so-called processor) 12 to which the scope 10 is detachably coupled, and a TV monitor 14 to which the image-signal-processing unit 12 is connected.

The scope 10 is representative of various types of scopes, used for bronchial, esophageal, gastro, colon, etc. inspections, and these various types of scopes use the image-signal-processing unit 12 in common. This is because the scope 10 is detachably coupled to the image-signal-processing unit 12.

The scope 10 is provided with a solid-state image sensor 16, such as a CCD (charge-coupled-device) image sensor, at the distal end thereof, and the CCD image sensor 16 is associated with an objective lens system (not shown). In this embodiment, the CCD image sensor 16 has an on-chip color filter (not shown), and thus an endoscope image is reproduced as a full color image on the TV monitor 14. The CCD image sensor 16 has a CCD driving-signal feeding line 18 and an image-signal feeding line 20 which are extended through the scope 10.

The scope 10 is further provided with a flexible optical light guide cable 22 extended therethrough and formed as a bundle of optical fibers. The optical light guide cable 22 terminates with a light-radiating end face at the distal end of the scope 10, and is associated with a lighting lens system (not shown) provided thereat. Also, the proximal end of the light guide cable 22 terminates with a rigid optical guide rod 24, which is optically connected to a suitable light source, as stated hereinafter.

Thus, an object to be sensed by the CCD image sensor 16 is illuminated by light radiating from the distal end of the optical light guide cable 22, and is focused as an endoscope image on a light-receiving surface of the CCD image sensor 16 by the objective lens system. The endoscope image is photoelectrically converted into a frame of color image-pixel signals due to the existence of the on-chip color filter. In this embodiment, the on-chip color filter of the CCD image sensor 16 is constituted so as to produce a frame of color image-pixel signals composed of a frame of red image-pixel signals, a frame of green image-pixel signals, and a frame of blue image-pixel signals.

The image-signal-processing unit 12 includes a system controller 26 which constitutes a microcomputer, used for controlling the electronic endoscope system as a whole, comprising a central processing unit (CPU), a read-only memory (ROM) for storing programs and constants, a random-access memory (RAM) for storing temporary data, and an input/output interface circuit (I/O).

The image-signal-processing unit 12 further includes a timing controller 28, an image-signal-processing circuit 30, and a character-generating circuit 32, which are operated under the control of the system controller 26. As shown in FIG. 1, when the coupling between the scope 10 and the unit 12 is established, the CCD driving-signal feeding line 18 and the image-signal feeding line 20 are connected to the timing controller 28 and the image-signal processing circuit 30, respectively.

The timing controller 28 outputs various series of clock pulses to control driving timing of various elements forming the electronic endoscope system. Namely, the various elements are sequentially and systematically driven in accordance with the various series of clock pulses output from the timing controller 28. For example, a series of clock pulses is fed as a CCD driving signal to the CCD image sensor 16 through the CCD driving-signal feeding line 18, and the color image-pixel signals are repeatedly and sequentially read from the CCD image sensor 16 in accordance with the series of clock pulses.

The image-signal-processing unit 12 processes the color image-pixel signals sequentially fed from the CCD image sensor through the image-signal feeding line 20, thereby producing a component-type video signal on the basis of the processed color image-pixel signals, as stated in detail hereinafter. As is well known, the component-type video signal is composed of red, green, and blue video signal components and a compound-synchronizing-signal component. The component-type video signal is then fed to the TV monitor 14, and the endoscope image, sensed by the CCD image sensor 16, is reproduced as a full color motion image on the TV monitor 14.

The character-generating circuit 32 generates character-pattern color (red, green, and blue) video signal components, and adds to the red, green and blue video signal components of the component-type video signal, to thereby display various character items on the TV monitor 14 together with the endoscope image. For example, the character items may be a patient's name, age, and ID number, a doctor's name, an examination date, a medical comment and so on. Also, according to this invention, the character items further involve an organ-region character item representing a distinctive region of an organ medically examined by the electronic endoscope system.

In this embodiment, the image-signal-processing unit 12 is provided with a light source device 34 which is operated under the control of the system controller 26. As shown in FIG. 1, when the coupling between the scope 10 and the image-signal-processing unit 12 is established, a free end face of the rigid optical guide rod 24 is optically connected to the light source device 34.

In particular, the light source device 34 includes a white light lamp, such as a halogen lamp, a xenon lamp or the like, a lamp power circuit for electrically energizing the white light source, and a diaphragm mechanism provided between the white light lamp and the free end face of the light guide rod 24. The lamp power circuit is operated under the control of the system controller 26 to control turn-ON and turn-OFF status of the white light lamp. The diaphragm mechanism is also operated under control of the system controller 26 to adjust an amount of light directed from the white light lamp onto the free end face of the light guide rod 24, i.e., the amount of illuminating-light radiating from the distal end of the optical light guide cable 22 can be regulated by the diaphragm mechanism, whereby a constant overall brightness of a reproduced endoscope image on the TV monitor 14 can be maintained.

The image-signal-processing unit 12 has a front panel 36 shown as a block in FIG. 1, and the front panel 36 is suitably attached to a front wall of a housing of the image-signal-processing unit 12. Various switches are provided on the front panel 36. Switches, which especially relate to the present invention, are a power ON/OFF switch, a lamp ON/OFF switch, and an organ-region-indication-mode selection switch.

When the power ON/OFF switch is turned ON, a power source circuit (not shown) of the image-signal-processing unit 12 is supplied with electric power from a commercial power network.

The lamp ON/OFF switch is provided for controlling the turn-ON and turn-OFF of the white light lamp of the light source device 36. Namely, when the lamp ON/OFF switch is turned ON, an ON signal or high-level signal is output from the lamp ON/OFF switch to the system controller 26, whereby the white light lamp of the light source device 36 is electrically energized by the lamp power circuit under control of the system controller 26. When the lamp ON/OFF switch is turned OFF, an OFF signal or low-level signal is output from the lamp ON/OFF switch to the system controller 26, whereby the electrical energization of the white light lamp is stopped under the control the system controller 26, thereby turning OFF the white light lamp.

The organ-region-indication-mode selection switch is provided for selecting an organ-region-indication mode. The mode selection switch constitutes a self-return switch, and a high-level signal is output as a pulse signal from the mode selection switch to the system controller 26 whenever being operated. When the power ON/OFF switch is turned ON, the organ-region-indication mode is not selected. When the high-level signal is output from the mode selection switch, the system controller 26 recognizes that the organ-region-indication mode has been selected. When the high-level signal is again output from the mode selection switch, the system controller 26 recognizes that the selection of the organ-region-indication mode has been cancelled. Namely, the selection of the organ-region-indication mode and the cancellation of the selection are alternately performed every operation of the mode selection switch.

The organ-region-indication-mode selection switch is associated with a pilot lamp provided on the front panel 36. The pilot lamp is lit when the organ-region-indication mode has been selected. The pilot lamp is turned OFF when the selection of the organ-region-indication mode has been cancelled. Thus, due to the existence of the pilot lamp, it can be easily confirmed whether the organ-region-indication mode has been selected.

Note, usually, while a doctor manipulates the scope 10, the switches, provided on the front panel 36, are operated by a suitable assistant, such as a nurse or the like, in accordance with the doctor's instructions.

Another organ-region-indication-mode selection switch, indicated by reference 38 in FIG. 1, may be provided on the scope 10. Of course, the mode selection switch 38 is intended to be operated by the doctor. Namely, the selection of the organ-region-indication mode and the cancellation of the selection can be carried out by the doctor. Preferably, the mode selection switch on the front panel 36 and the mode selection switch 38 on the scope 10 are correlated with each other. Namely, for example, when the organ-region-indication mode is selected by operating the mode selection switch on the front panel 36, it is possible to cancel the selection of the organ-indication mode by operating the mode selection switch 38, and vice versa.

Note, although not illustrated in FIG. 1, the mode selection switch 38 is connected to the system controller 26 when establishing the coupling between the scope 10 and the image-signal-processing unit 12.

As shown in FIG. 1, the image-signal-processing unit 12 is provided with a keyboard 40 which is connected to the system controller 26 to input various commands and various data to the system controller 26. A function, pertaining to the organ-region-indication-mode selection switch (38), may be allocated to a suitable function key on the keyboard 40. When the selection of the organ-region-indication mode is performed by the function key or mode selection key on the keyboard 40, the mode selection switch may be eliminated from the front panel 36. Preferably, the mode selection key is also correlated with the aforesaid mode selection switches. Namely, for example, when the organ-region-indication mode is selected by operating the mode selection key, it is possible to cancel the selection of the organ-indication mode by operating one of the aforesaid mode selection switches, and vice versa.

Note, the keyboard 40 is also operated by a suitable assistant, such as a nurse or the like while the doctor manipulates the scope 10.

Figure 2:
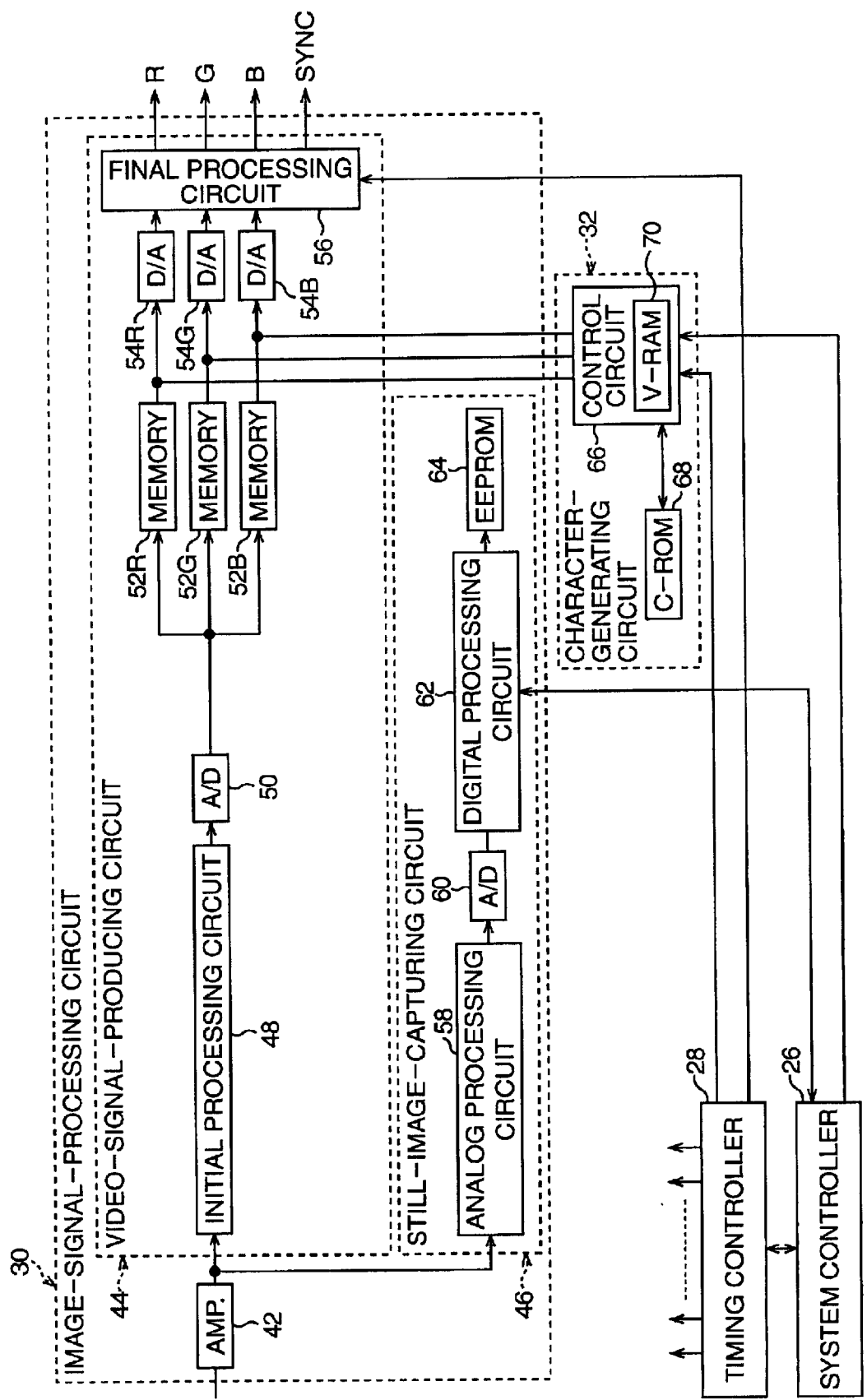
FIG. 2 is a detailed block diagram of an image-signal-processing unit of the electronic endoscope system.

FIG. 2 shows a detailed block diagram of the image-signal processing circuit 30. As shown in this drawing, the image-signal-processing circuit 30 includes a preamplifier 42, a video-signal-producing circuit 44, and a still-image-capturing circuit 46. The color image-pixel signals, read from the CCD image sensor 16, are input to the preamplifier 42 in which each image-pixel signal is amplified with a predetermined amplification factor. Then, the amplified color image-pixel signals are input in parallel from the preamplifier 42 to both the video-signal-producing circuit 44 and the still-image-capturing circuit 46.

The video-signal-producing circuit 30 includes an initial processing circuit 48, and an analog-to-digital (A/D) converter 50, frame memories 52R, 52G, and 52B, digital-to-analog (D/A) converters 54R, 54G, and 54B, and a final processing circuit 56.

The color image-pixel signals, input to the video-signal-producing circuit 44, are suitably processed in the initial processing circuit 48. For example, the color image-pixel signals are subjected to noise-reduction, gamma-correction, white-balance correction, black-level-clamping and so on. The processed image-pixel signals are then converted into color digital image-pixel signals, i.e., red, green and blue digital image-pixel signals, by the A/D converter 50, and the red, green and blue digital image-pixel signals are temporarily stored in the frame memories 52R, 52G, and 52B, respectively.

Note, in FIG. 2, although the initial processing circuit 48, the A/D converter 50, and the frames memories 52R, 52G, and 52B are not connected to the timing controller 28, the processing of the image-pixel signals in the initial processing circuit 48, the conversion of the color analog image-pixel signals into the color digital image-pixel signals in the A/D converter 50, and the storage of the color digital image-pixel signal in the frame memories 52R, 52G, and 52B are sequentially and systematically performed in accordance with a series of clock pulses output from the timing controller 28.

While the red, green and blue digital image-pixel signals are successively stored in the frame memories 52R, 52G, and 52B, the respective red, green and blue digital image-pixel signals are simultaneously read from the frame memories 52R, 52G, and 52B in accordance with a series of clock pulses output from the timing controller 28, and are output as red, green and blue digital video signal components to the D/A converters 54R, 54g, and 54B, in which the red, green and blue digital video signal components are respectively converted into red, green and blue analog video signal components. The red, green and blue analog video signal components are suitably processed in the final processing circuit 56. For example, the red, green and blue analog video signal components are subjected to high-frequency-noise reduction, amplification and so on.

The processed red, green and blue analog video signal components are output from the final processing circuit 56, and are fed from the video-signal-producing circuit 44 to the TV monitor 14, as represented by references R, G, and B. On the other hand, the timing controller 28 produces a compound synchronizing-signal component, and outputs it to the final processing circuit 56. The compound synchronizing-signal component is output from the final processing circuit 56 together with red, green and blue analog video signal components, and is fed from the video-signal-producing circuit 44 to the TV monitor 14, as represented by reference SYNC.

In short, the component-type analog video signal, composed of the color video signal components R, G, and B, and the compound-synchronizing-signal component SYNC, is produced in the video-signal-producing circuit 44, and is fed to the TV monitor 14, on which the endoscope image is reproduced as a full color motion image in accordance with the component-type video signal.

Note, the conversion of the color digital video signal components into the color analog video signal components in the D/A converters 54R, 54G, and 54B, and the processing of the color analog video signal components in the final processing circuit 56 are sequentially and systematically performed in accordance with series of clock pulses output from the timing controller 28.

As shown in FIG. 2, the still-image-capturing circuit 46 includes an analog processing circuit 58, an analog-to-digital (A/D) converter 60, a digital processing circuit 62, and a memory 64. The digital processing circuit 62 includes a microcomputer comprising a central processing unit (CPU), a read-only memory (ROM) for storing programs and constants, a random-access memory (RAM) for storing temporary data, and an input/output interface circuit (I/O). The memory 64 comprises a suitable non-volatile memory, such as an electrically erasable programmable read only memory (EEPROM).

The memory or EEPROM 64 stores an organ-region-image data base constituted on the basis of a specific organ map, for example, a bronchus map.

Figure 3:
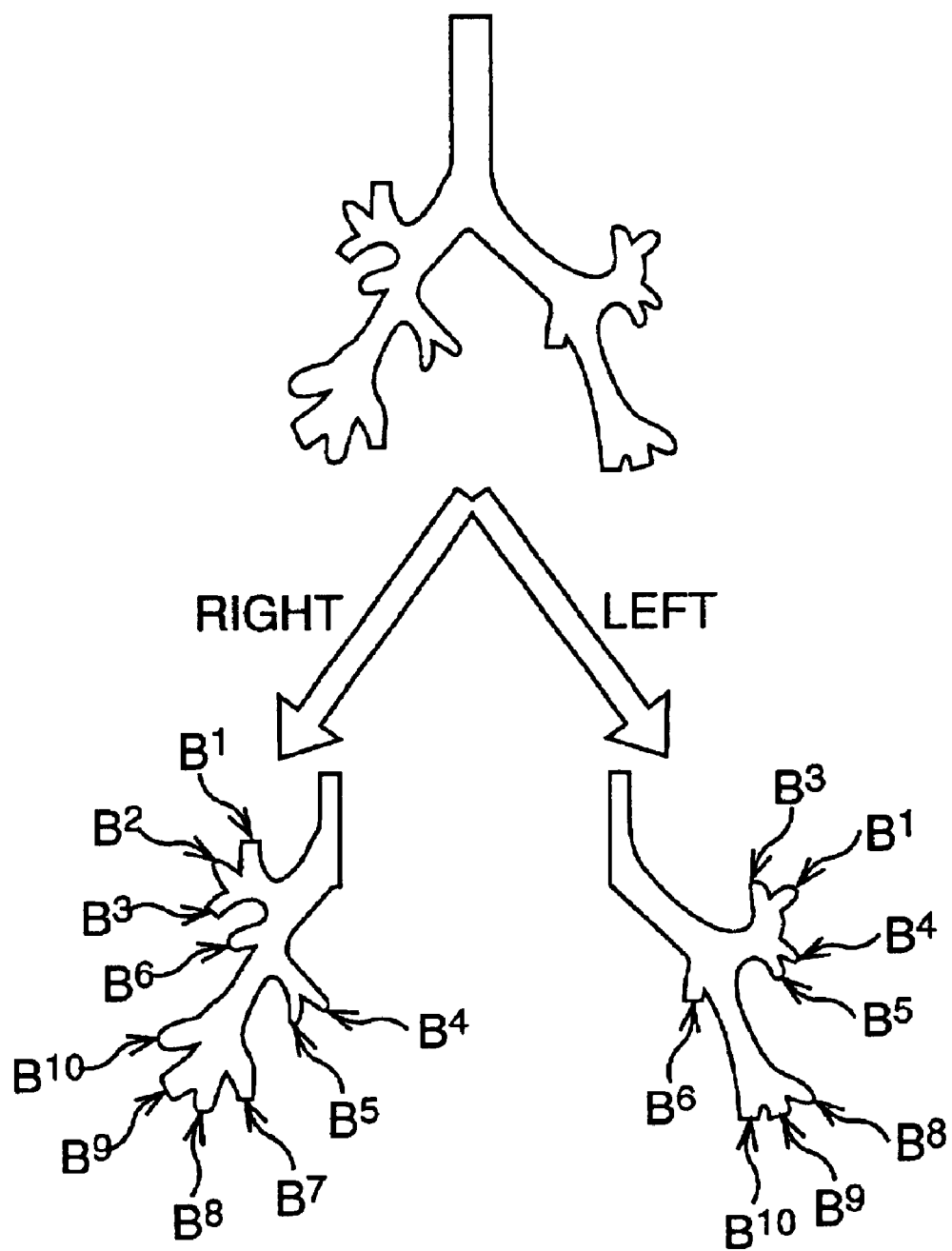
FIG. 3 is a schematic view for explaining a bronchus map.

With reference to FIG. 3, the bronchus map, in which respective distinctive regions of the bronchus are represented by the established and fixed references, is illustrated by way of example.

In particular, as is apparent from FIG. 3, the bronchus comprises right and left main branches, and each of the right and left main branches includes distinctive subordinate branches extending therefrom, as represented by references $B^1$ to $B^{10}$. Note, in FIG. 3, the distinctive subordinate branches of the left main branch which should be represented by references $B^2$ and $B^7$ are not visible, and thus no references to $B^2$ and $B^7$ are used in the left main branch. Also, although not illustrated in FIG. 3, each of the distinctive subordinate branches $B^1$ to $B^{10}$ has further-subordinate branches which are also distinctive, extending therefrom, and the further-subordinate branches are represented by established references. For example, further-subordinate branches, extended from the subordinate branch $B^6$, are represented by references $B^6a$, $B^6b$, $B^6c$, . . . , and further-subordinate branches, extended from the subordinate branch $B^{10}$, are represented by references $B^{10}a$, $B^{10}b$, $B^{10}c$, . . . . Among doctors, the established references ($B^1$ to $B^{10}$; $B^1a$, $B^1b$, $B^1c$, . . . ; $B^2a$, $B^2b$, $B^2c$, . . . ; $B^9a$, $B^9b$, $B^9c$, . . . ; and $B^{10}a$, $B^{10}b$, $B^{10}c$, . . . ) are utilized to specify and identify a distinctive region of the bronchus.

With reference to FIG. 4, a bronchus-region-image data base, stored in the memory or EEPOM 64, is conceptually shown, and is constituted on the basis of the bronchus map shown in FIG. 3.

The bronchus-region-image data base comprises a right-main-branch-image data base section and a left main-branch-image data base section. Each of the data base sections includes a plurality of image-data storage areas, and a number of image-data storage areas corresponds to the number of the established references ($B^1$ to $B^{10}$; $B^1a$, $B^1b$, $B^1c$, . . . ; $B^2a$, $B^2b$, $B^2c$, . . . ; $B^9a$, $B^9b$, $B^9c$, . . . ; and $B^{10}a$, $B^{10}b$, $B^{10}c$, . . . ).

The right-main-branch-image data base section includes a plurality of image-data storage areas, and the respective image-data storage areas have headers for storing character code data corresponding to organ-region character items R-$B^1$ to R-$B^{10}$; R-$B^1a$, R-$B^1b$, R-$B^1c$, . . . ; R-$B^2a$, R-$B^2b$, R-$B^2c$, . . . ; R-$B^9a$, R-$B^9b$, R-$B^9c$, . . . ; and R-$B^{10}a$, R-$B^{10}b$, R-$B^{10}c$, . . . . The head characters "R" of the organ-region character items mean that these items relate to the right main branch of the bronchus. For example, when image data, representing a junction of the subordinate branch $B^2$ of the right main branch, is stored in one of the image-data storage areas, the character code data corresponding to the organ-region character item R-$B^2$ is stored in the header of the image-data storage area concerned, and, when image data, representing a junction of the further-subordinate branch $B^6b$ of the right main branch, is stored in another one of the image-data storage areas, the character code data corresponding to the organ-region character item R-$Bb^6$ is stored in the header of the other image-data storage area concerned.

Similarly, the left-main-branch-image data base section includes a plurality of image-data storage areas, and the respective image-data storage areas have headers for storing character code data corresponding to organ-region character items $L\text{-}B^1$ to $L\text{-}B^{10}$; $L\text{-}B^1a$, $L\text{-}B^1b$, $L\text{-}B^1c$, . . . ; $L\text{-}B^2a$, $L\text{-}B^2b$, $L\text{-}B^2c$, . . . ; $L\text{-}B^9a$, $L\text{-}B^9b$, $L\text{-}B^9c$, . . . ; and $L\text{-}B^{10}a$, $L\text{-}B^{10}b$, $L\text{-}B^{10}c$, . . . . The head characters "L" of the organ-region character items mean that these items relate to the left main branch of the bronchus. For example, when image data, representing a junction of the subordinate branch $B^2$ of the left main branch, is stored in one of the image-data storage areas, the character code data corresponding to the organ-region character item $L\text{-}B^2$ is stored in the header of the image-data storage area concerned, and, when image data, representing a junction of the further-subordinate branch $B^6b$ of the left main branch, is stored in another one of the image-data storage areas, the character code data corresponding to the organ-region character item $L\text{-}Bb^6$ is stored in the header of the other image-data storage area concerned.

Note, in this embodiment, each of the junctions of the subordinate and further-subordinate branches ($B^1$ to $B^{10}$; $B^1a$, $B^1b$, $B^1c$, . . . ; $B^2a$, $B^2b$, $B^2c$, . . . ; $B^9a$, $B^9b$, $B^9c$, . . . ; and $B^{10}a$, $B^{10}b$, $B^{10}c$, . . . ) is handled as a distinctive region of the bronchus.

Image data, stored in each image-data storage area, derives from still image data of a junction of a corresponding subordinate or further-subordinate branch, obtained during an actual medical examination using the electronic endoscope system. In particular, all image data to be stored in the respective image-data storage areas of the bronchus-region-image data base are processed and prepared on the basis of the past-recorded bronchus image data, using an image-processing computer, and the prepared image data are stored in the respective image-data storage areas of the bronchus-region-image data base by, for example, connecting the image-processing computer to the system controller 26 of the image-signal processing unit 12. Namely, the prepared image data are fed from the image-processing computer to the system controller 26, and are then written in the EEPROM 64 through the digital processing circuit 62.

With reference to FIG. 5, the processing of still image data, which is performed by the image-processing computer, is conceptually shown by way of example. In FIG. 5, reference A1 indicates an original still image based on the still image data, and the still image A1 represents the junction of the subordinate branch $B^{10}$ of the left main branch. The still image A1 is subjected to two-level quantization with a suitable threshold, thereby producing a binary image A2. Then, the binary image A2 is subjected to feature-extraction, such as edge-extraction, thereby producing a feature-extracted image A3. Subsequently, the feature-extracted image A2 is subjected to normalization, thereby producing a normalized image A4, with a given size. Thus, image data of the normalized image A4 is stored in the image-data storage area headed "$L\text{-}B^{10}$".

Note, in this embodiment, each of the image-data storage areas of the data base has a capacity for storing five frames of image data, and at least one frame of image data is previously stored in each of the image-data storage areas.

The color image-pixel signals, input from the preamplifier 42 to the still-image-capturing circuit 46, are suitably processed in the analog processing circuit 58, which is similar to the initial processing circuit 48 of the video-signal-producing circuit 44. Namely, in the analog processing circuit 58, the color image-pixel signals are subjected to noise-reduction, gamma-correction, white-balance correction, black-level-clamping and so on. Then, the processed color image-pixel signals are converted into color digital image-pixel signals, i.e., red, green, and blue digital image-pixel signals, by the A/D converter 60.

While the organ-region-indication mode is selected by operating either the mode selection switch on the front panel 36, the mode selection switch 38 on the scope 10, or the mode selection key on the keyboard 40, a frame of color digital image-pixel signals is retrieved as a frame of still image data from the A/D converter 60 by the digital processing circuit 62 at a suitable regular time interval, for example, 1 second. The retrieved still image data are processed as explained with reference to FIG. 5, and the processed still image data is temporarily stored as referential image data in the RAM of the digital processing circuit 62. Then, the digital processing circuit 62 searches the bronchus-region-image data base of EEPROM 64 for image data which coincides with the referential image data.

In particular, in the digital processing circuit 62, image data is successively read from the bronchus-region-image data base (EEPROM 64), and the read image data is compared with the referential image data, using, for example, a well-known pattern matching method, to numerically evaluate a degree of coincidence between the read image data and the referential image data. In this embodiment, the degree of coincidence between the read image data and the referential image data is represented by a percentage. For example, if the degree of coincidence between the read image data and the referential image data is more than a percentage threshold (e.g., 80%), it is determined that there is a significant coincidence between the read image data and the referential image data. In this embodiment, the percentage threshold is adjustable, as stated in detail hereinafter.

When there is the coincidence between the read image data and the referential image data, character code data is read from the header associated with the read image data, and is fed from the digital processing circuit 62 to the system controller 26. Then, the system controller 26 outputs the character code data to the character-generating circuit 32, to display a character item on the TV monitor 14, based on the character code data.

In particular, as shown in FIG. 2, the character-generating circuit 32 includes a control circuit 66 and a character ROM (C-ROM) 68. The control circuit 66 is formed as a microcomputer having a video RAM (V-RAM) 70.

When the character code data is output from the system controller 26 to the character-generating circuit 32, the character code data is written in a predetermined address of the V-RAM 70 by the control circuit 66, and is then output to the C-ROM 68, in which the character code data is converted into character-pattern signal data. The control circuit 32 produces digital red, green and blue character-pattern video signal components from the character-pattern signal data, and then outputs them to the output lines for the digital red, green and blue video signal components, extending from the frame memories 52R, 52G and 52B, whereby the digital red, green and blue character-pattern video signal components are added to the digital red, green and blue video signal components. The output timing of the digital red, green and blue character-pattern video signal components from the control circuit 66 is controlled in accordance with a series of clock pulses output from the timing controller 28. Thus, the character item is displayed on the TV monitor 14 at a predetermined location, on the basis of the added character-pattern video signal components.

Figure 6:
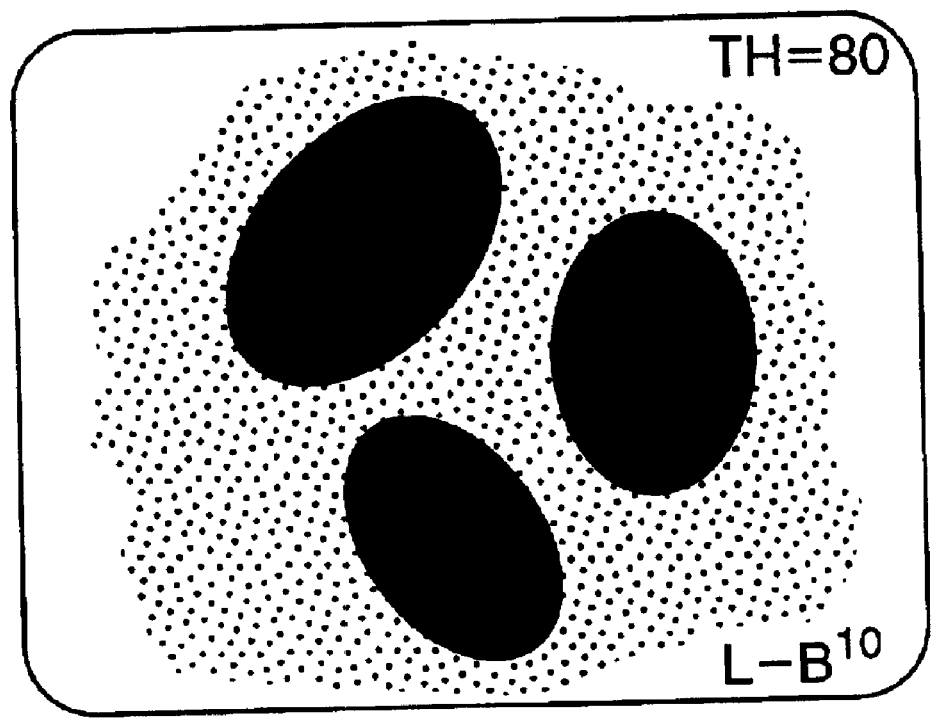
FIG. 6 is a view showing by way of example a screen of a TV monitor of FIG. 1.

An address in the v-RAM 70, to which each character code data is written, corresponds to a location on the TV monitor 14, at which a character item corresponding to each character code data, is displayed. Thus, for example, the character code data, corresponding to the organ-region character item L-B$^{10}$, is written to predetermined addresses in the V-RAM 70, the organ-region character item L-B$^{10}$ is displayed on the TV monitor 14 at a predetermined location, as shown in FIG. 6.

Figure 7:
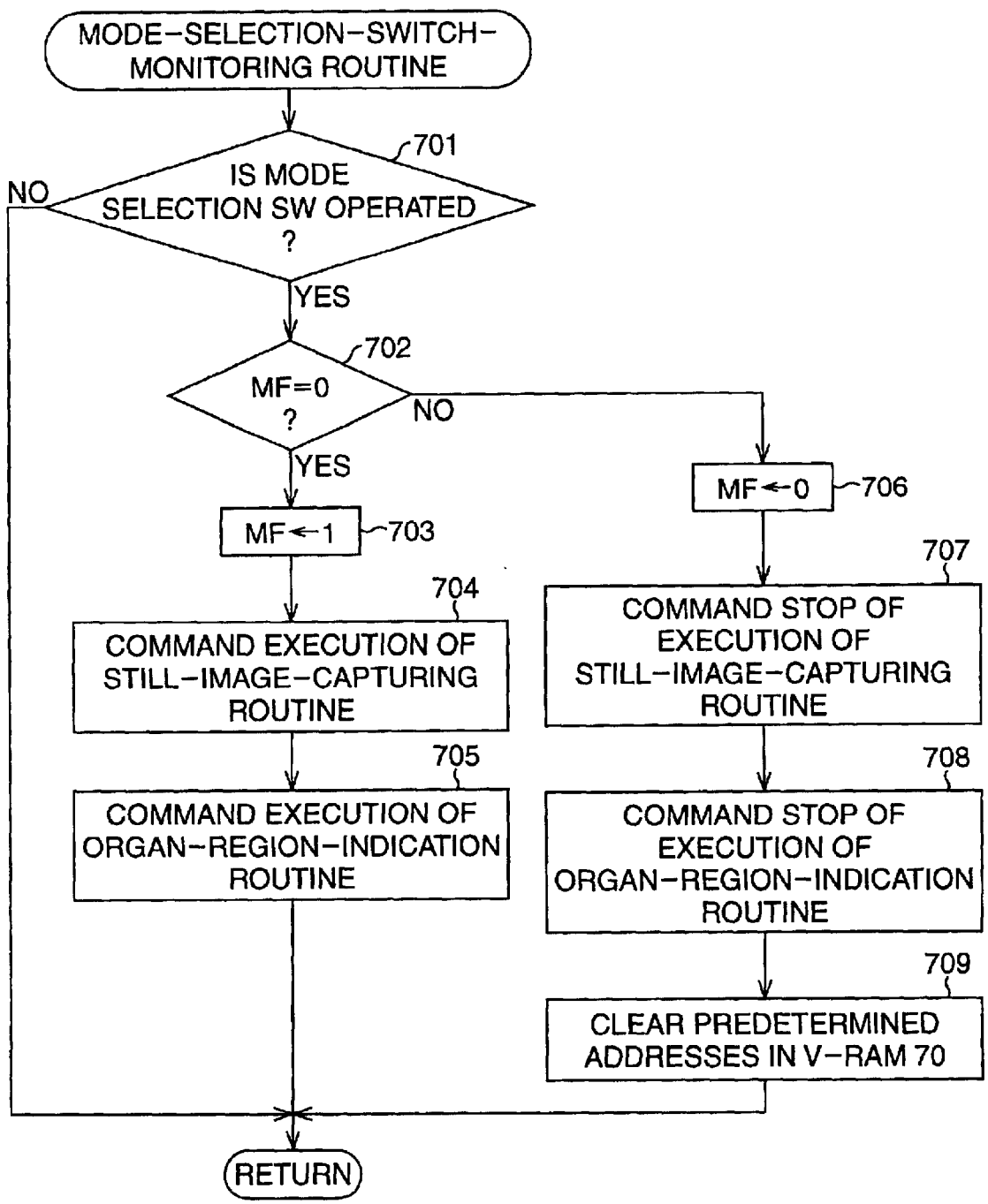
FIG. 7 is a flowchart of a mode-selection-switch-monitoring routine executed in a system controller shown in FIGS. 1 and 2.

FIG. 7 shows a flowchart of a mode-selection-switch-monitoring routine which is formed as a time-interruption routine executed in the system controller 26 at regular suitable intervals, for example, 20 ms. Note, the execution of the mode-selection-switch-monitoring routine is started after an initialization-routine of the image-signal-processing unit 12 is executed by turning ON the power ON/OFF switch, and is repeated every 20 ms as long as the image-signal-processing unit 12 is powered ON.

In step 701, it is monitored whether the mode selection switch on the front panel 36, the mode selection switch 38 on the scope 10, or the mode selection key on the key board 40 has been operated. When it is confirmed that neither the mode selection switches or the mode selection key has been operated, the routine immediately ends. Thereafter, although the routine is repeatedly executed every 20 ms, there is no progress until one of the mode selection switches or the mode selection key is operated.

In step 701, when it is confirmed that one of the mode selection switches or the mode-selection key has been operated, the control proceeds to step 702, in which it is determined whether a mode-selection flag MF is "0" or "1". The flag MF is provided for recognizing whether the organ-region-indication-mode is selected. Namely, if MF=0, it is recognized that the organ-region-indication-mode is not selected, and, if MF=1, it is recognized that the organ-region-indication-mode is selected. Note, the flag MF is initialized to "0" in the execution of the initialization-routine of the image-signal-processing unit 12.

In step 702, if MF=0, the control proceeds to step 703, in which the flag MF is changed from "0" to "1", whereby it is recognized that the organ-region-indication-mode has been selected. Then, in step 704, the system controller 26 feeds a command signal to the digital processing circuit 62 to start an execution of a still-image-capturing routine, and, in step 705, the system controller 26 commands an execution of an organ-region-indication routine to start.

Note, the still-image-capturing routine is explained in detail hereinafter with reference to FIGS. 12 and 13, and the organ-region-indication routine is explained in detail hereinafter with reference to FIG. 14.

In step 702, if MF=1, i.e. if the organ-region-indication mode is selected, the control proceeds from 702 to step 706, in which the flag MF is changed from "1" to "0", whereby it is recognized that the selection of the organ-region-indication-mode has been cancelled. Then, in step 707, the system controller 26 feeds a command signal to the digital processing circuit 62 to stop the execution of the still-image-capturing routine, and, in step 708, the system controller 26 commands the execution of the organ-region-indication routine to stop.

In step 709, the predetermined addresses in the V-RAM 70, for writing the character code data corresponding to any one of the organ-region character items is cleared. Thus, if an organ-region character item is displayed on the TV monitor 14, the display of the organ-region character item disappears.

Figure 8:
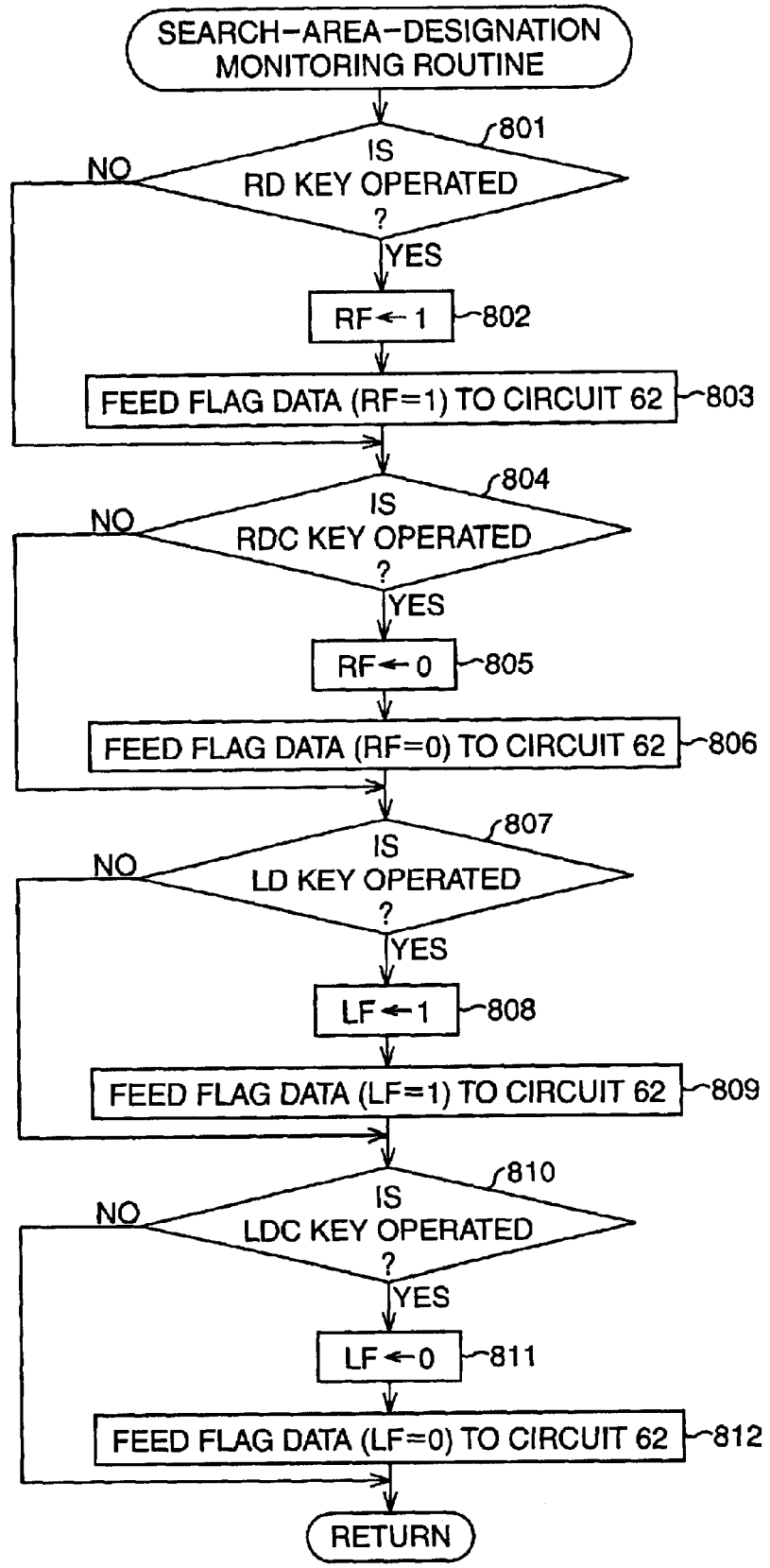
FIG. 8 is a flowchart of a search-area-designation-monitoring routine executed in the system controller shown in FIGS. 1 and 2.

FIG. 8 shows a flowchart of a search-area-designation-monitoring routine which is provided for monitoring whether an area to be searched is designated in the organ-region-image data base (FIG. 4). The search-area-designation-monitoring routine is also formed as a time-interruption routine executed in the system controller 26 at regular suitable intervals, for example, 20 ms. Note, the execution of the search-area-designation-monitoring routine is also started after the initialization-routine of the image-signal-processing unit 12 is executed by turning ON the power ON/OFF switch, and is repeated every 20 ms as long as the image-signal-processing unit 12 is powered ON.

In step 801, it is monitored whether a function key on the keyboard 40, which is allocated as a right-designation key, has been operated to designate the right-main-branch-region-image data base section of the bronchus-region-image data base (FIG. 4) as an area to be searched.

In step 801, when the operation of the right-designation key is confirmed, the control proceeds to step 802, in which a right-designation flag RF is set to "1", whereby it is recognized that the area to be searched is limited to the right-main-branch-region-image data base section. Then, in step 803, the system controller 26 feeds the flag RF as a flag data (RF=1) to the digital processing circuit 62.

In step 804, it is monitored whether a function key on the keyboard 40, which is allocated as a right-designation-canceling key has been operated to cancel the designation of the right-main-branch-region-image data base section as the area to be searched. Note, in step 801, when the operation of the right-designation key has not been confirmed, the control skips steps 802 and 803 and goes directly to step 804.

In step 804, when the operation of the right-designation-cancellation key is confirmed, the control proceeds to step 805, in which the right-designation flag RF is set to "0", whereby it is recognized that the designation of the right-main-branch-region-image data base section as the area to be searched has been cancelled. Then, in step 806, the system controller 26 feeds the flag RF as a flag data (RF=0) to the digital processing circuit 62. Note, in step 804, when the operation of the right-designation-cancellation key has not been confirmed, the control skips steps 805 and 806 and goes directly to step 807.

In step 807, it is monitored whether a function key on the keyboard 40, which is allocated as a left-designation key, has been operated to designate the left-main-branch-region-image data base section of the bronchus-region-image data base (FIG. 4) as an area to be searched.

In step 807, when the operation of the left-designation key is confirmed, the control proceeds to step 808, in which a left-designation flag LF is set to "1", whereby it is recognized that the area to be searched is limited to the left-main-branch-region-image data base section. Then, in step 809, the system controller 26 feeds the flag LF as a flag data (LF=1) to the digital processing circuit 62.

In step 810, it is monitored whether a function key on the keyboard 40, which is allocated as a left-designation-canceling key has been operated to cancel the designation of the left-main-branch-region-image data base section as the area to be searched. Note, in step 807, when the operation of the left-designation key has not been confirmed, the control skips steps 808 and 809 and goes directly to step 810.

In step 810, when the operation of the left-designation-cancellation key is confirmed, the control proceeds to step 811, in which the left-designation flag RF is set to "0", whereby it is recognized that the designation of the left-main-branch-region-image data base section as the area to be searched has been cancelled. Then, in step 812, the system controller 26 feeds the flag LF as a flag data (LF=0) to the digital processing circuit 62. Note, in step 810, when the operation of the left-designation-cancellation key is not confirmed, the control skips steps 811 and 812.

In short, when searching the bronchus-region-image data base by using the digital processing circuit 62, if RF=1, and if LF=0, the area to be searched is limited to the right-main-branch-region-image data base section, and, if RF=0, and if LF=1, the area to be searched is limited to the left-main-branch-region-image data base section.

Figure 9:
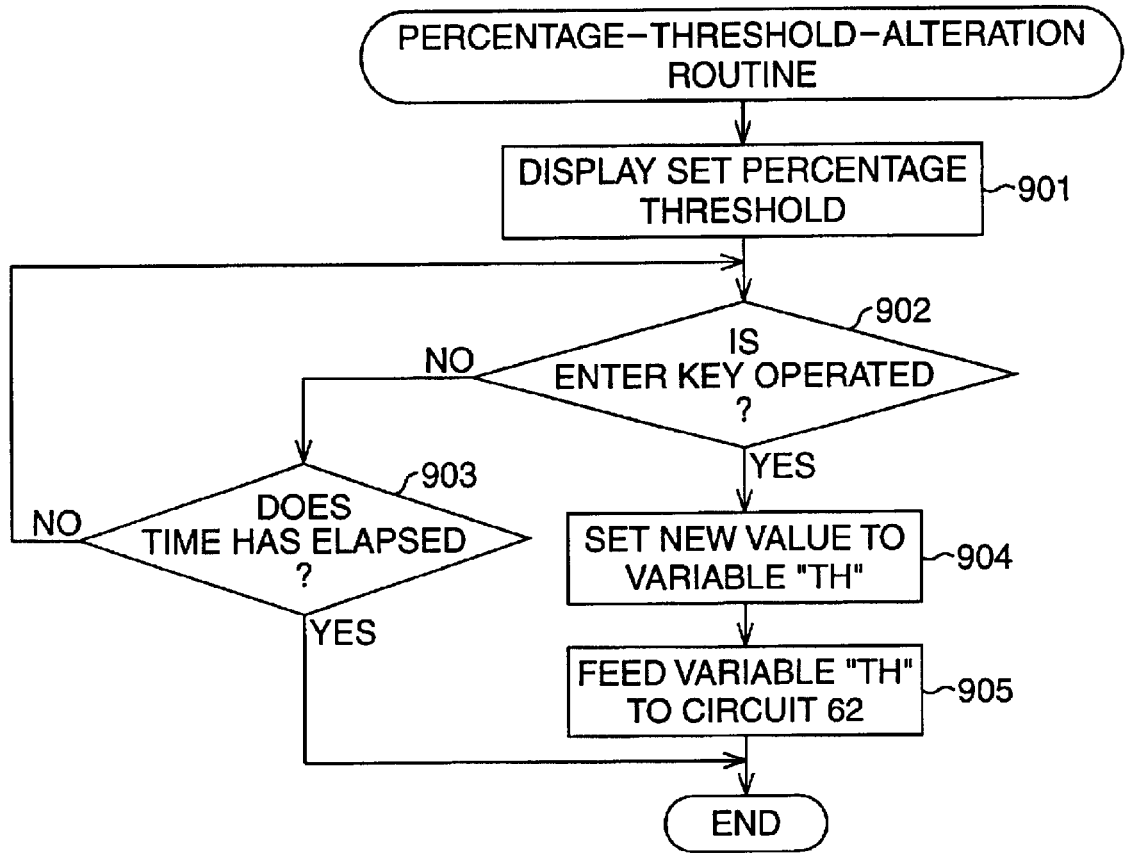
FIG. 9 is a flowchart of a percentage-threshold-alteration routine executed in the system controller shown in FIGS. 1 and 2.

FIG. 9 shows a flowchart of a percentage-threshold-alteration routine which is executed in the system controller 26. This routine is provided for altering the percentage-threshold used to determine whether image data read from the bronchus-region-image data base (EEPROM 64) coincides with referential image data, obtained from the A/D converter 60 and processed in the digital processing circuit 62. To start an execution of the percentage-threshold-alteration routine, a function key on the keyboard 40 is utilized. Namely, by operating the function key concerned or routine-start key, the routine is only executed once.

In step 901, the set percentage threshold is displayed on the TV monitor 14. As shown in FIG. 6 by way of example, if the percentage threshold is set to 80%, a character item "TH=80" is displayed on the TV monitor 14.

Of course, in order to display the character item "TH=80" on the TV monitor 14, character code data corresponding to the character item "TH=80" must be written in predetermined addresses in the V-RAM 70. The character item "TH=80" is composed of a fixed item portion "TH=", and a variable item portion "80". Fixed code data corresponding to the fixed item portion "TH=" is previously stored in the ROM of the system controller 26. Variable code data corresponding to the variable item portion "80" is temporarily stored in the RAM of the system controller 26, and can be changed, using numeral-inputting keys on the keyboard 40.

In short, when the routine-start key on the keyboard 40 is operated, the fixed item portion "TH=" and the variable item portion "80" are read from the respective ROM and RAM of the system controller 26, and are combined with each other and written in the predetermined addresses in the V-RAM 70, resulting in the display of the character item "TH=80" on the TV monitor 14 (step 901).

In step 902, it is monitored whether the enter key on the keyboard 40 is operated. When the operation of the enter key on the keyboard 40 is not confirmed, the control proceeds to step 903, in which it is determined whether a predetermined time period of, for example, three minutes has elapsed. When the three minutes has not elapsed, the control returns to step 902.

During the elapse of the three minutes, it is desired that a new percentage threshold is input by operating the numeral-inputting keys on the keyboard 40, and that the enter key on the keyboard 40 is then operated after the input of the new percentage threshold. For example, when "85" is input as the new percentage threshold, and when the enter key is then operated, the control proceeds from step 902 to step 904, in which a variable TH, representing the percentage threshold, is set from the old value "80" to the new value "85". Then, in step 905, the system controller 26 feeds the variable TH (85) to the digital processing circuit 62, and the routine ends.

In step 904, while the value of the variable TH is changed from "80" to "85", a character code data corresponding to a character item "85" is substituted for the character code data, corresponding to the character item "80", stored in the RAM of the system controller 26, whereby the displayed character item "TH=80" is changed to a character item "TH=85".

In step 903, when it is confirmed that the three minutes has elapsed without operation of the enter key on the keyboard 40 (step 902), the routine immediately ends, and thus the value of the variable TH cannot be changed.

Figure 10:
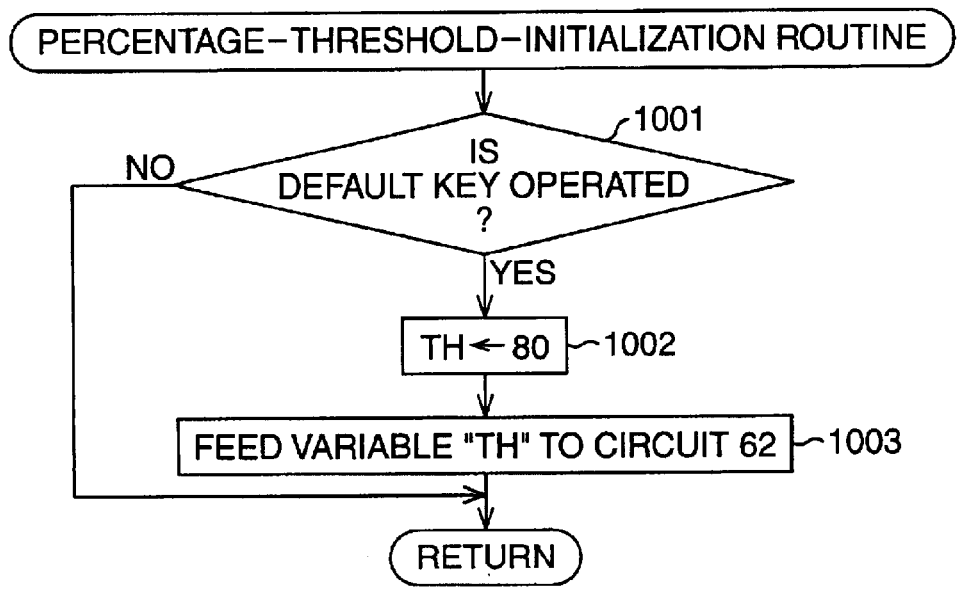
FIG. 10 is a flowchart of a percentage-threshold-initialization routine executed in the system controller shown in FIGS. 1 and 2.

FIG. 10 shows a flowchart of a percentage-threshold-initialization routine which is provided for forcibly initializing the percentage threshold. This initialization routine is formed as a time-interruption routine executed in the system controller 26 at regular suitable intervals, for example, 20 ms. Note, the execution of the percentage-threshold-initialization routine is started after the initialization-routine of the image-signal-processing unit 12 is executed by turning ON the power ON/OFF switch, and is repeated every 20 ms as long as the image-signal-processing unit 12 is powered ON.

In step 1001, it is monitored whether a function key on the keyboard 40, which is allocated as a default key, has been operated. When the operation of the default key is not confirmed, the routine immediately ends. Thereafter, although the routine is repeatedly executed every 20 ms, there is no progress until the default key is operated.

In step 1001, when the operation of the default key is confirmed, the control proceeds to step 1002, in which an initial value, which may be, for example, "80", is forcibly set to the variable TH. Then, in step 1003, the system controller 26 feeds the variable TH (80) to the digital processing circuit 62, and the routine ends.

Note, the variable TH is initialized to "80" in the execution of the initialization-routine of the image-signal-processing unit 12. Also, note, the character item, representing the percentage threshold, displayed on the TV monitor 14, is changed to "TH=80", whenever the variable TH is initialized to "80".

Figure 11:
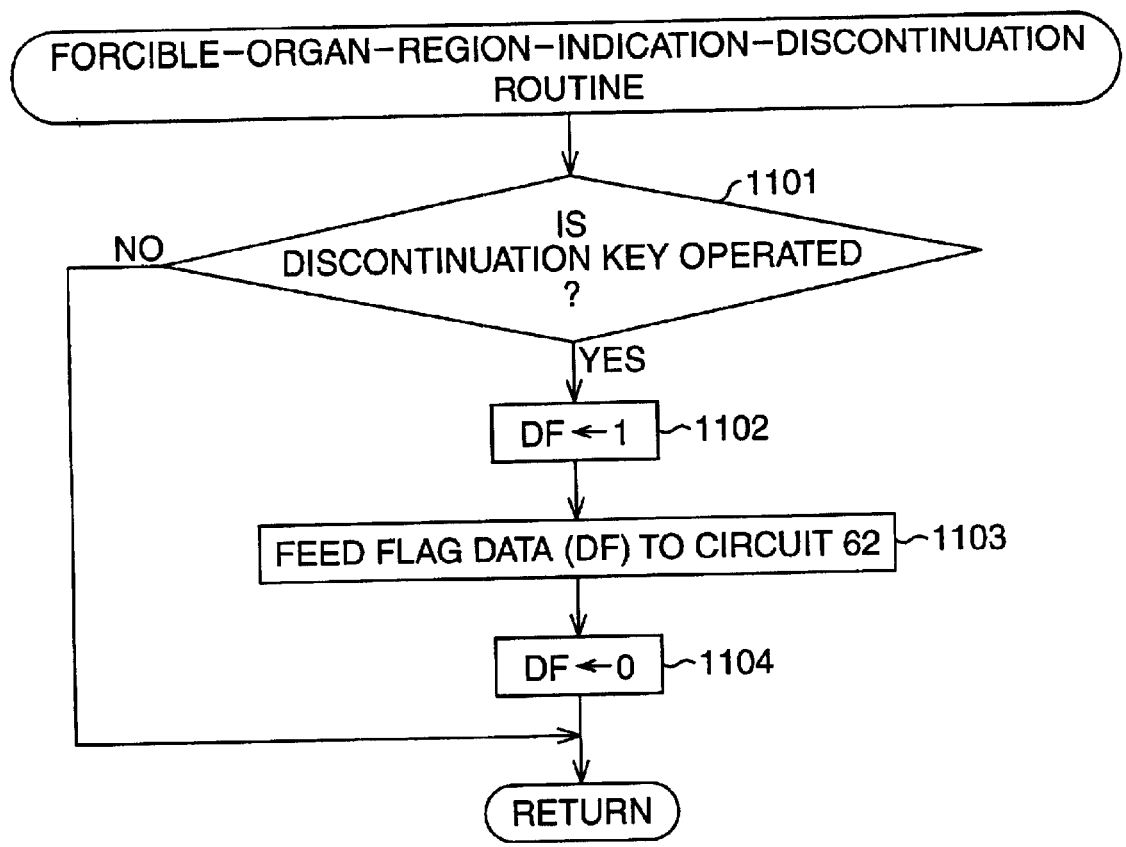
FIG. 11 is a flowchart of a forcible-organ-region-indication-discontinuation routine executed in the system controller shown in FIGS. 1 and 2.

FIG. 11 shows a flowchart of the forcible-organ-region-indication-discontinuation routine which is provided for forcibly discontinuing the display of an organ-region character item on the TV monitor 14. This routine is also formed as a time-interruption routine executed in the system controller 26 at regular suitable intervals, for example, 20 ms. Note, the execution of the routine is started after the execution of the initialization-routine of the image-signal-processing unit 12, and is repeated every 20 ms as long as the image-signal-processing unit 12 is powered ON.

In step 1101, it is monitored whether a function key on the keyboard 40, which is allocated as a discontinuation key for discontinuing display of an organ-region character item on the TV monitor 14 has been operated. When the operation of the discontinuation key is not confirmed, the routine immediately ends. Thereafter, although the routine is repeatedly executed every 20 ms, there is no progress until the discontinuation key is operated.

In step 1101, when it is confirmed that the discontinuation key has been operated, the control proceeds to step 1102, in which a discontinuation flag DF is set to "1". The flag DF is provided for recognizing whether the display of the organ-region character item on the TV monitor 14 is forcibly discontinued. Namely, if DF=0, it is recognized that the display of the organ-region character item on the TV monitor 14 is continued, and, if DF=1, it is recognized that the display of the organ-region character item on the TV monitor 14 is discontinued. Note, the flag DF is initialized to "0" in the execution of the initialization-routine of the image-signal-processing unit 12.

In step 1103, the system controller 26 feeds the flag DF as a flag data (DF=1) to the digital processing circuit 62. Then, in step 1104, the flag DF is initialized to "0" in the system controller 26, and the routine once ends.

In short, in the execution of the forcible-organ-region-indication-discontinuation routine, it is monitored whether the discontinuation key has been operated, and the flag data (DF=1) is fed from the system controller 26 to the digital processing circuit 62 whenever the discontinuation key is operated.

Figure 12:
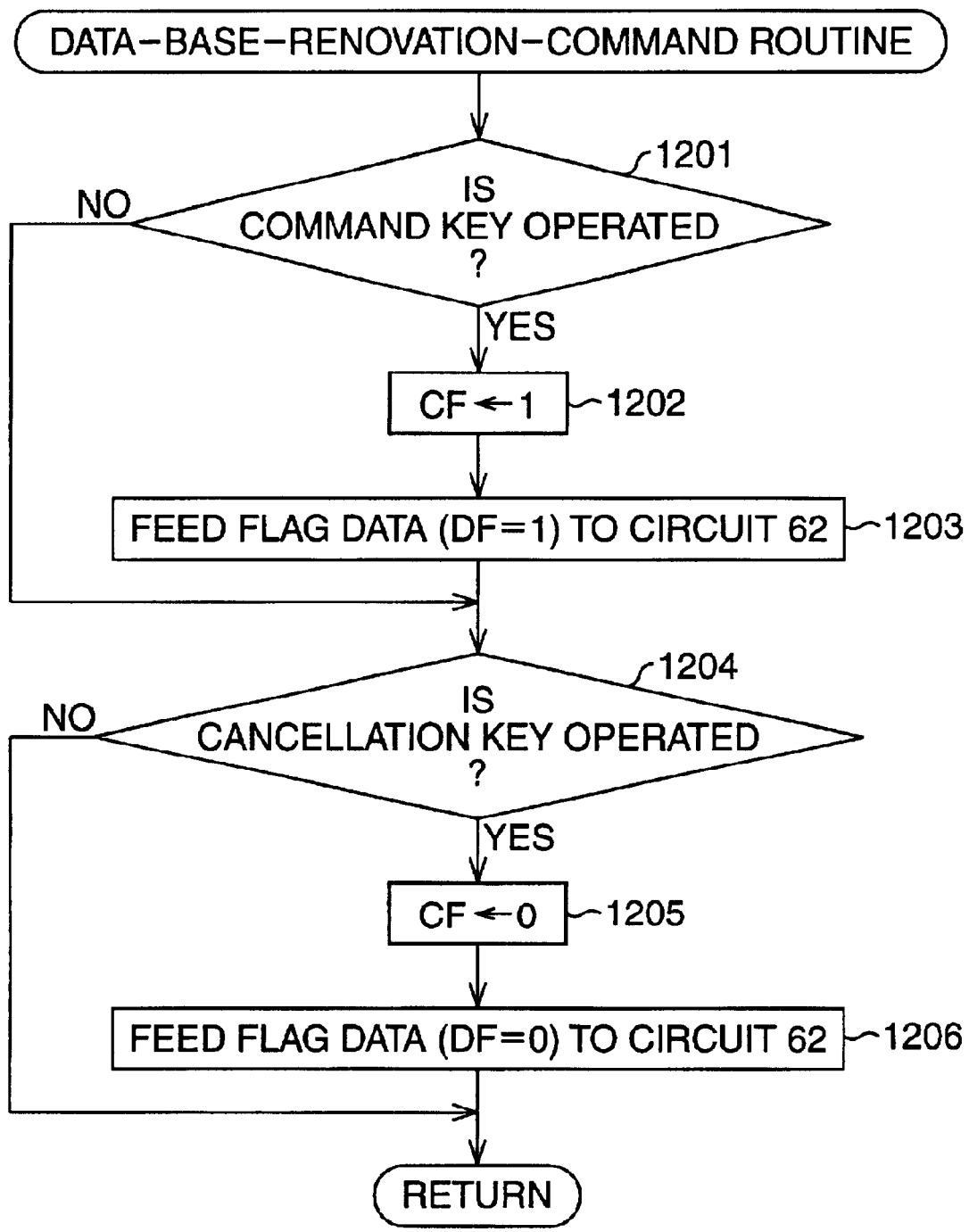
FIG. 12 is a flowchart of a data-base-renovation-command routine executed in the system controller shown in FIGS. 1 and 2.

FIG. 12 shows a flowchart of a data-base-renovation-command routine which is provided for commanding the digital processing circuit 62 to determine whether the bronchus-region-image data base should be renovated when there is a significant coincidence between referential image data obtained from the A/D converter 60 and image data read from the bronchus-region-image data base. The renovation command routine is also formed as a time-interruption routine executed in the system controller 26 at regular suitable intervals, for example, 20 ms. Note, the execution of the renovation command routine is started after the execution of the initialization-routine of the image-signal-processing unit 12, and is repeated every 20 ms as long as the image-signal-processing unit 12 is powered ON.

In step 1201, it is monitored whether a function key on the keyboard 40, which is allocated as a renovation-command key for renovating the bronchus-region-image data base, has been operated.

In step 1201, when it is confirmed that the renovation-command key has been operated, the control proceeds to step 1202, in which a renovation-command flag CF is set to "1". Then, in step 1203, the system controller 26 feeds the flag CF as a flag data (CF=1) to the digital processing circuit 62.

The flag CF is provided for recognizing whether the digital processing circuit 62 is commanded to renovate the bronchus-region-image data base. Namely, if CF=0, it is recognized that there is no command to renovate the data base, and, if CF=1, it is recognized that there is a command to renovate the data base. Note, the flag CF is initialized to "0" when the initialization-routine of the image-signal-processing unit 12 is executed.

In step 1204, it is monitored whether a function key on the keyboard 40, which is allocated as a renovation-cancellation key for canceling the renovation of the bronchus-region-image data base, has been operated. When the operation of the renovation-cancellation key has been confirmed, the control proceeds to step 1205, in which the renovation-command flag CF is initialized to "0". Then, in step 1206, the system controller 26 feeds the flag CF as a flag data (CF=0) to the digital processing circuit 62.

When the operation of both the command and cancellation keys is not confirmed (steps 1201 and 1204), the routine ends. Thereafter, although the routine is repeatedly executed every 20 ms, there is no progress until either the command key or the cancellation key is operated.

In short, in the execution of the data-base-renovation-command routine, it is monitored whether either the command key or the cancellation key has been operated. Whenever the command key is operated, the flag data (CF=1) is fed from the system controller 26 to the digital processing circuit 62. Whenever the cancellation key is operated, the flag data (CF=0) is fed from the system controller 26 to the digital processing circuit 62.

Figure 13:
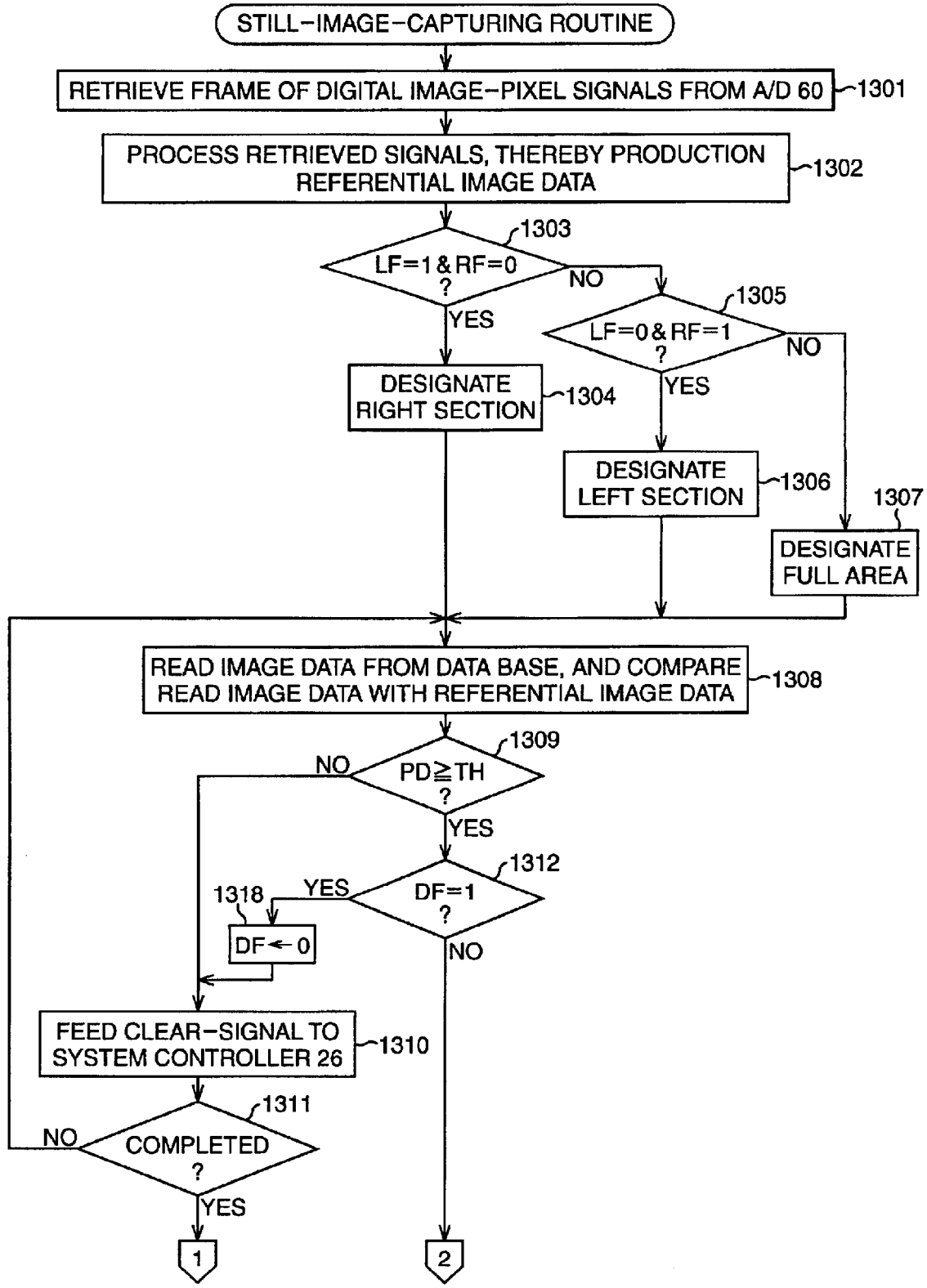
FIG. 13 is a part of a flowchart of a still-image-capturing routine executed in a digital processing circuit shown in FIG. 2.
Figure 14:
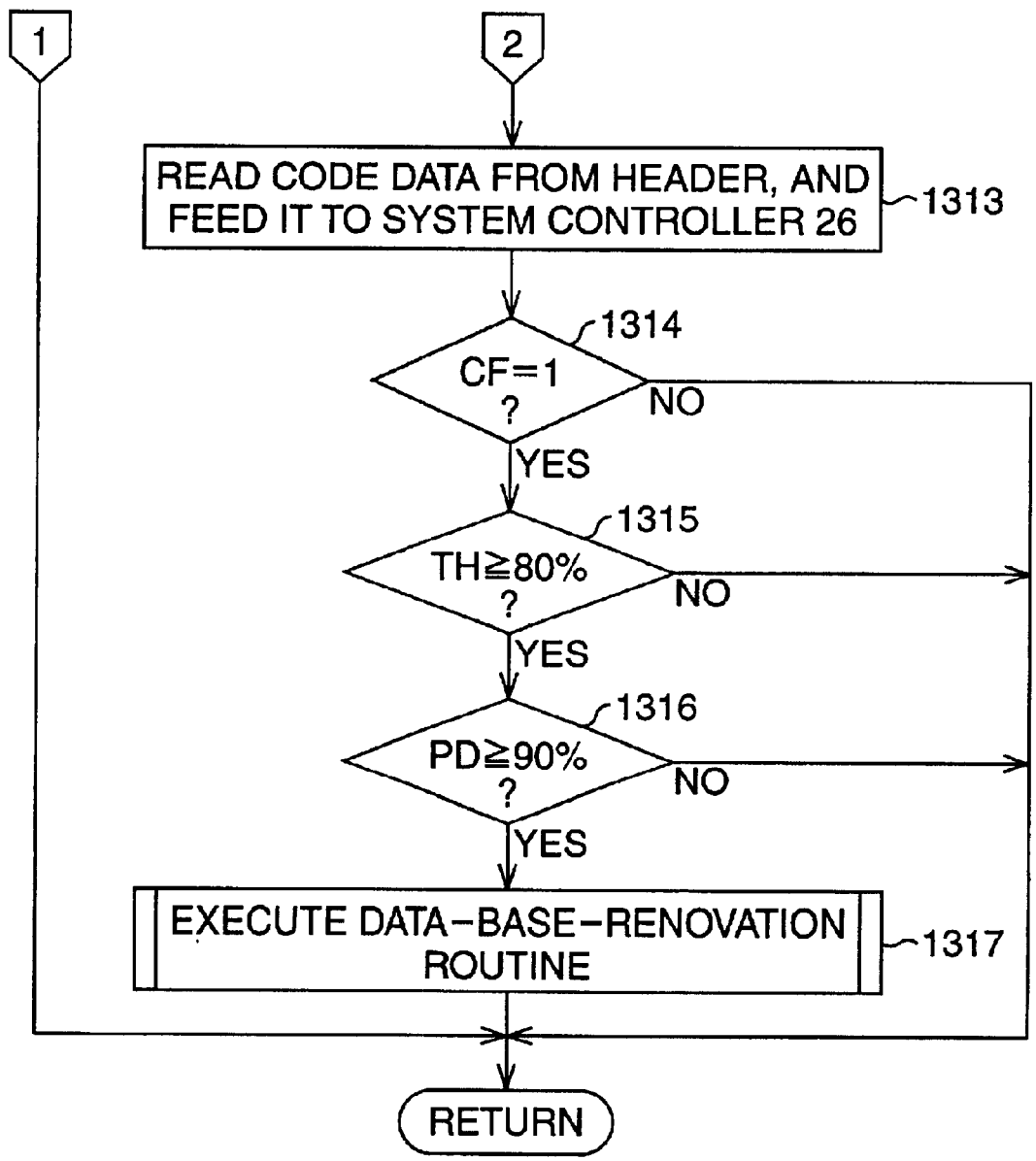
FIG. 14 is the remaining part of the flowchart of the still-image-capturing routine shown in FIG. 13.

FIGS. 13 and 14 show a flowchart of the still-image-capturing routine which is referred to in steps 704 and 707 of the mode-selection-switch-monitoring routine (FIG. 7). The still-image-capturing routine is formed as a time-interruption routine executed in the digital processing circuit 62 at regular suitable intervals, for example, 1 second. As is apparent from the explanation of FIG. 7, the execution of the still-image-capturing routine is started when selecting the organ-region-indication mode (MF=1), and the execution of the still-image-capturing routine ends when canceling the selection of the organ-region-indication mode (MF=0).

In step 1301, a frame of color digital image-pixel signals is retrieved as a still image from the A/D converter 60. Then, in step 1302, the retrieved color digital image-pixel signals are processed as explained with reference to FIG. 5, thereby producing referential image data. Note, the produced referential image data is temporarily stored in the RAM of the digital processing circuit 62.

In step 1303, it is determined whether the respective flags RF and LF are set to "1" and "0". If RF=1, and if LF=0, the control proceeds to step 1304, in which the right-main-branch-region-image data base section of the bronchus-region-image data base (FIG. 4) is designated as an area to be searched.

In step 1303, if RF≠1, and if LF≠0, the control proceeds from step 1303 to step 1305, in which it is determined whether the respective flags RF and LF are set to "0" and "1". If RF=0, and if LF=1, the control proceeds to step 1306, in which the left-main-branch-region-image data base section of the bronchus-region-image data base (FIG. 4) is designated as an area to be searched.

In step 1305, if RF≠0, and if LF≠1, i.e. if both the flags RF and LF are "0" or if both the flags RF and LF are "1", the control proceeds from step 1305 to step 1307, in which it is determined whether the respective flags RF and LF are set to "0" and "1", in which a full area of the bronchus-region-image data base is designated as an area to be searched.

Note, there may be a case where both the right-designation key and the left-designation key are mistakenly operated in order to designate the full area of the bronchus-region-image data base as an area to be searched (RF=1 and LF=1).

At any event, in step 1308, image data is read from the designated area of the bronchus-region-image data base, and the read image data is compared with the referential image data, using the pattern matching method, whereby a degree of coincidence between the read image data and the referential image data is numerically evaluated. As already stated hereinbefore, in this embodiment, the degree of coincidence between the read image data and the referential image data is represented by a percentage, and the percentage is temporarily stored as percentage data PD in the RAM of the digital processing circuit 62.

In step 1309, it is determined whether the percentage data PD is more than the percentage threshold TH. If PD<TH, the control proceeds to step 1310, in which a clear-signal is fed from the digital processing circuit 62 to the system controller 26.

As will be explained hereinafter, when the clear-signal is received by the system controller 26, the addresses in the V-RAM 70, for writing the character code data corresponding to any one of the organ-region character items, is cleared. Thus, if an organ-region character item is being displayed on the TV monitor 14, the organ-region character item disappears.

In step 1311, it is determined whether the search of the designated area of the bronchus-region-image data base has been completed. If the search is still not completed, the control returns to step 1308, in which image data is further read from the designated area of the bronchus-region-image data base. When the search is completed for all the image data, read from the designated area of the bronchus-region-image data base, and when no coinciding with the referential image data exist (PD<TH), the routine ends.

In step 1309, if PD≧TH, i.e. if a read image data coincides with the referential image data, the control proceeds from step 1309 to step 1312, in which it is determined whether the flag DF is "1" or "0". If DF=0, i.e. if the display of an organ-region character item on the TV monitor 14 is not forcibly discontinued, the control proceeds to step 1313, in which a character code data is read from the header associated with the read image data concerned, and the read character code data is fed to the system controller 26. As soon as the character code data is received by the system controller 26, the received character code data is output to the character-generating circuit 32 to display an organ-region character item, corresponding to the character code data, on the TV monitor 14.

In step 1314, it is determined whether the renovation-command flag CF is "1" or "0". If CF=1, i.e., if the renovation of the bronchus-region-image data base is commanded, the control proceeds to step 1315, in which it is determined whether the percentage threshold TH is more than 80%. If TH≧80%, the control proceeds to step 1316, in which it is determined whether the percentage data PD is more than 90%. If PD≧90%, i.e. if the degree of coincidence between the read image data and the referential image data is more than 90%, the control proceeds to step 1317, in which a data-base-renovation routine is executed as a subroutine, whereby the referential image data is added to the bronchus-region-image data base (FIG. 4), as will be stated in detail hereinafter with reference to FIG. 16.

In short, in this embodiment, only when the percentage-threshold TH is set to more than 80% (step 1315), and only when the degree of coincidence between the read image data and the referential image data is more than 90% (step 1316), is the data-base-renovation routine executed to add the referential image to the bronchus-region-image data base. In other words, although the renovation of the bronchus-region-image data base is commanded (CF=1), the referential image data cannot be added to the bronchus-region-image data base under the conditions of TH<80% and PD<90%.

In step 1312, if the discontinuation flag DF is "1", i.e. if the display of an organ-region character item on the TV monitor 14 is forcibly discontinued, the control proceeds from step 1312 to 1318, in which the discontinuation flag is initialized to "0". Then, in step 1310, a clear-signal is fed from the digital processing circuit 62 to the system controller 26, whereby the display of the organ-region character item on the TV monitor 14 is forcibly cancelled.

For example, when the setting of the percentage threshold TH is too low (e.g., 70%), there may be a case where an organ-region-character item, displayed on the TV monitor 14, does not correctly indicates an organ-region displayed as an endoscope image thereon. In this situation which may be perceived by a skilful doctor, the display of the organ-region-character item on the TV monitor 14 can be forcibly discontinued by operating the discontinuation key on the keyboard 40 (step 1101 of FIG. 11).

Figure 15:
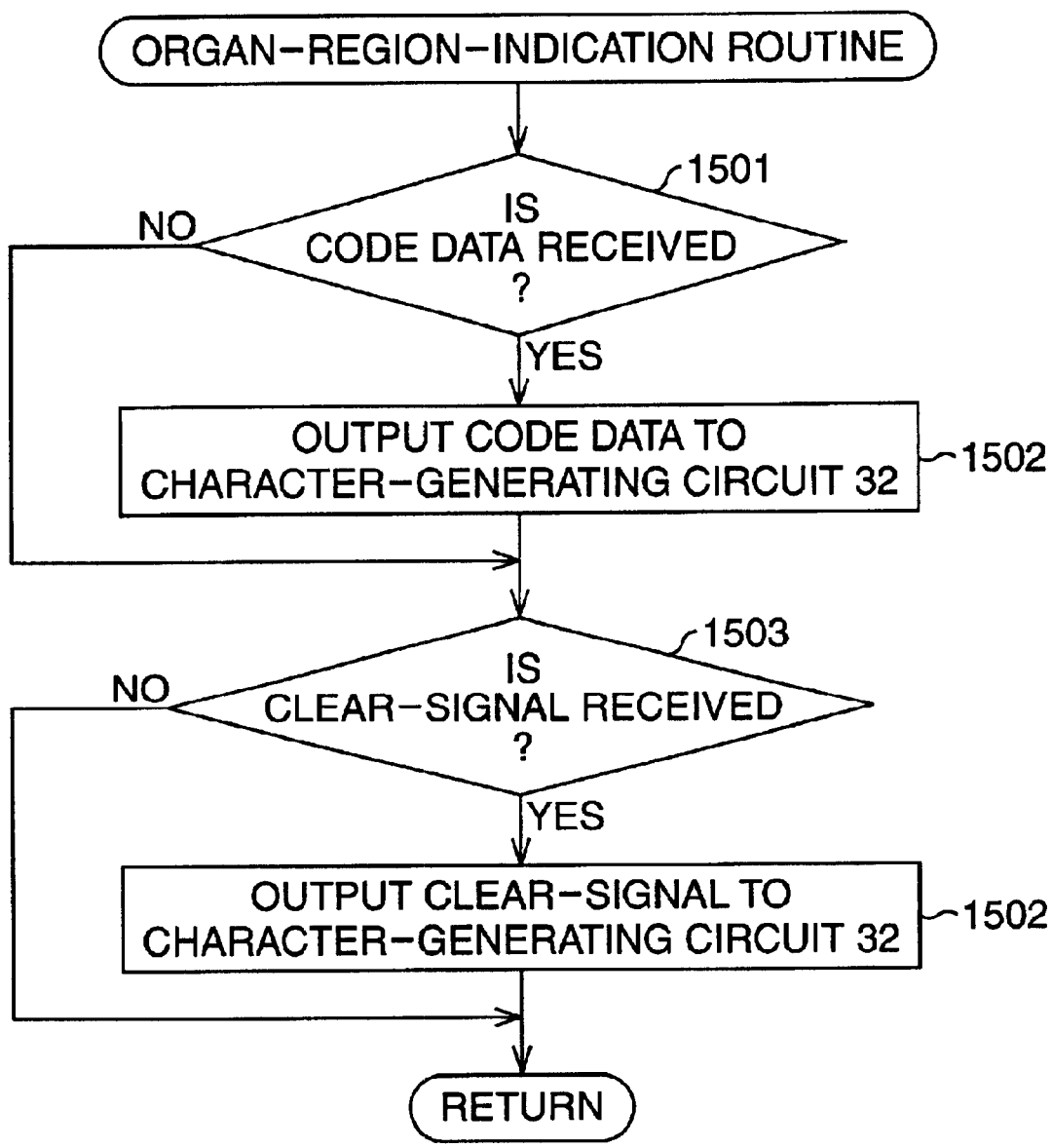
FIG. 15 is a flowchart of an organ-region-indication routine executed in the system controller shown in FIGS. 1 and 2.

FIG. 15 shows a flowchart of the organ-region-indication routine referred to in steps 705 and 708 of the mode-selection-switch-monitoring routine (FIG. 7). The organ-region-indication routine is formed as a time-interruption routine executed in the system controller 26 at regular suitable intervals, for example, 1 second. As is apparent from the explanation of FIG. 7, the execution of the organ-region-indication routine is started when selecting the organ-region-indication mode (MF=1), and the execution of the organ-region-indication routine ends when canceling the selection of the organ-region-indication mode (MF=0).

In step 1501, it is monitored whether a character code data has been received from the digital processing circuit 62 (step 1313 of FIG. 14). When the receipt of the character code data is not confirmed, the control skips step 1502 and goes to step 1503, in which it is monitored whether a clear-signal has been received from the digital processing circuit 62 (step 1310 of FIG. 13). When the receipt of the clear-signal is not confirmed, the routine ends. Thereafter, although the routine is repeatedly executed every 1 second, there is no progress until either the character code data or the clear-signal is received from the digital processing circuit 62.

In step 1501, when the receipt of the character code data is confirmed, the control proceeds to step 1502, in which the character code data is output to the character-generating circuit 32. The input character code data is written in the predetermined addresses in the V-RAM 70 by the control circuit 66, whereby an organ-region character item, corresponding to the character code data, is displayed on the TV monitor 14.

Thus, during medical examination of a patient's bronchus with a bronchial scope (10), for example, when the distal end of the bronchial scope reaches the junction of the subordinate branch $B^{10}$ of the left main branch, an endoscope image of that junction, displayed on the TV monitor 14, is indicated by the organ-region character item $L\text{-}B^{10}$ displayed thereon, as shown in FIG. 6. It is therefore possible for a doctor to correctly and quickly determine what region of the bronchus the distal end of the bronchial scope has reached.

In step 1503, when the receipt of the clear-signal is confirmed, the control proceeds to step 1504, in which the clear-signal is output to the character-generating circuit 32. When the clear-signal is received by the character-generating circuit 32, the predetermined addresses in the V-RAM 70, in which the character code data corresponding to the organ-region character item concerned is written, is cleared by the control circuit 66, whereby the display of the organ-region character item on the TV monitor 14 disappears.

Figure 16:
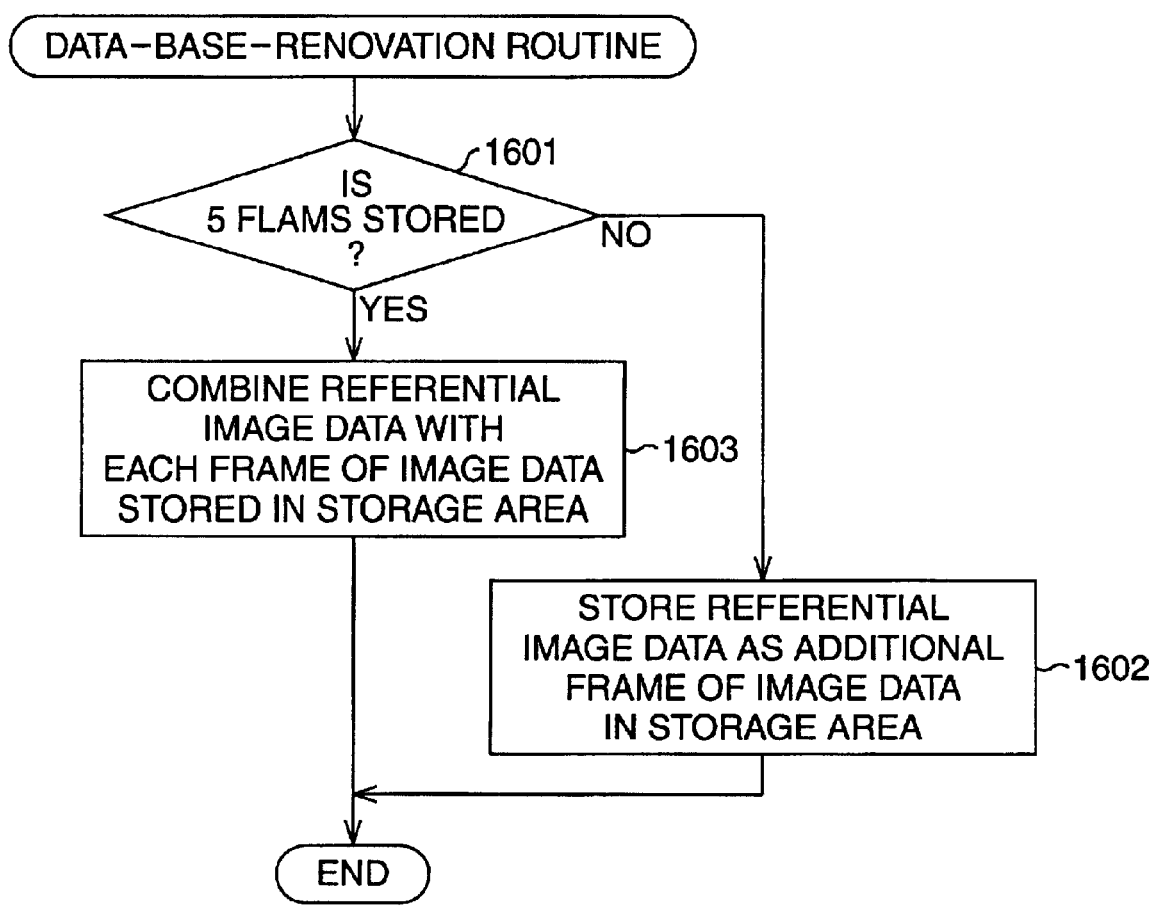
FIG. 16 is a flowchart of a data-base-renovation routine executed as a subroutine during the execution of the still-image-capturing routine shown in FIGS. 13 and 14.

FIG. 16 shows a flowchart of the data-base-renovation routine executed in step 1317 of the still-image-capturing routine of FIGS. 13 and 14.

In step 1601, it is determined whether five frames of image data are stored in the image-data storage area concerned of the bronchus-region-image data base. Note, as stated hereinbefore, each image-data storage area of the data base has the capacity for storing five frames of image data. Also, note, the frame of image data, read from the image-data storage area concerned, exhibits a degree of coincidence more than 90% with respect to the referential image data concerned (step 1316 of FIG. 14).

In step 1601, if it is confirmed that a number of frames of image data stored in the image-data storage area concerned is less than four, the control proceeds to step 1602, in which the referential image data concerned is additionally stored as a new frame of image data in the image-data storage area concerned.

On the other hand, in step 1601, if it is confirmed that a number of the frames of image data stored in the image-data storage area concerned is five, the control proceeds to step 1603, in which the referential image data is combined with each of the five frames of image data, and is then processed such that a frame of average image data is produced from the combined image data. Namely, all pixel data, included in the referential image data, are correspondingly added to all pixel data included in each frame of image data, and average image data is produced from each added pixel data. In short, each of the five frames of image data is renovated on the basis of the referential image data. Optionally, in step 1603, any one of the five frames of image data may be substituted for the referential image data.

During operation of the electronic endoscope system, while renovating the bronchus-region-image data base by executing the data-base-renovation routine, it is possible to enrich the bronchus-region-image data base, resulting in improvement of the reliability of the organ-region-indication system.

In the aforesaid embodiment, although the bronchus-region-image data base, based on the bronchus map, is constituted in the EEPROM 64, another organ-region-image data base may be constituted in the EEPROM 64, it too being based on a specific organ map. Finally, it will be understood by those skilled in the art that the foregoing description is of a preferred embodiment of the system, and that various changes and modifications may be made to the present invention without departing from the spirit and scope thereof.

The disclosure relates to subject matters contained in Japanese Patent Application No. 2001-054048 (filed on Feb. 28, 2001) which is expressly incorporated herein, by reference, in its entirety.

What is claimed is:

1. An organ-region-indication system incorporated in an electronic endoscope system in which an endoscope image is displayed as a motion image on a monitor in accordance with a video signal produced therein, said indication system comprising:

an organ-region-image data base, constituted on the basis of an organ map, in which a plurality of reference data indicating distinctive organ-regions of said organ map and a plurality of image data representing said distinctive organ-regions are correspondingly stored;

a still-image-capturing system that retrieves a frame of still image data as referential image data from the video signal at suitable regular time intervals;

a searching system that searches said organ-region-image data base for image data which coincides with said referential image data after the retrieval of the frame of still image data from said video signal by said still-image-capturing system; and a reference-data-display-control system that displays corresponding reference data on said monitor only when the image data, which coincides with the referential image data, is found by said searching system, whereby an endoscope image displayed as the motion image on said monitor is indicated by said corresponding reference data displayed thereon.

2. An organ-region-indication system as set forth in claim 1, wherein said reference-data-display-control system comprises a canceling system that cancels a preceding display of the reference data on said monitor when the image data, which coincides with the referential image data, is not found by said searching system.

3. An organ-region-indication system as set forth in claim 1, wherein said reference-data-display-control system comprises a forcible-canceling system that forcibly cancels a display of reference data on said monitor even if the image data, which coincides with the referential image data, is found by said searching system.

4. An organ-region-indication system as set forth in claim 1, wherein said searching system comprises a searching-area-designating system in which an area to be searched is designated in said organ-region-image data base.

5. An organ-region-indication system as set forth in claim 1, further comprising a data-base-renovating system that renovates said organ-region-image data base on the basis of the referential image data when the image data coincides with the referential image data.

6. An organ-region-indication system as set forth in claim 1, wherein said searching system comprises:

a reading system that reads image data in succession from said organ-region-image data base; and a determining system that determines whether the read image data coincides with said referential image data.

7. An organ-region-indication system as set forth in claim 6, wherein said determining system comprises:

a numerical-evaluating system that numerically evaluates a degree of coincidence between the read image data and the referential image data; and a comparison system that compares the degree of coincidence with a threshold, thereby determining that there is a coincidence between the read image data and the referential image data when the degree of coincidence is more than said threshold, and thereby determining that there is no coincidence between the read image data and the referential image data when the degree of coincidence is less than said threshold.

8. An organ-region-indication system as set forth in claim 7, wherein said determining system further comprises a threshold-altering system that alters a value of said threshold.

9. An organ-region-indication system as set forth in claim 1, wherein each image data, to be stored in said organ-region-image data base, is subjected to feature-extraction, and the referential image data is subjected to the same feature-extraction as each image data.

* * * * *